US010278736B2

(12) United States Patent
Samdani et al.

(10) Patent No.: US 10,278,736 B2
(45) Date of Patent: May 7, 2019

(54) METHODS AND TECHNIQUES FOR SPINAL SURGERY

(71) Applicant: SHRINERS HOSPITALS FOR CHILDREN, Tampa, FL (US)

(72) Inventors: Amer Samdani, Wayne, PA (US); Randal R. Betz, Ocean City, NJ (US)

(73) Assignee: SHRINERS HOSPITALS FOR CHILDREN, Tampa, FL (US)

( * ) Notice: Subject to any disclaimer, the term of this patent is extended or adjusted under 35 U.S.C. 154(b) by 116 days.

(21) Appl. No.: 14/855,147

(22) Filed: Sep. 15, 2015

(65) Prior Publication Data

US 2016/0000468 A1 Jan. 7, 2016

Related U.S. Application Data

(63) Continuation of application No. PCT/US2014/028016, filed on Mar. 14, 2014.

(60) Provisional application No. 61/791,982, filed on Mar. 15, 2013.

(51) Int. Cl.
*A61B 17/70* (2006.01)

(52) U.S. Cl.
CPC ...... *A61B 17/7022* (2013.01); *A61B 17/7053* (2013.01); *A61B 17/7077* (2013.01); *A61B 17/7079* (2013.01); *A61B 17/7086* (2013.01); *A61B 17/7091* (2013.01)

(58) Field of Classification Search
CPC .............. A61B 17/70–17/7046; A61B 17/7074–17/7092
See application file for complete search history.

(56) References Cited

U.S. PATENT DOCUMENTS

| 4,271,836 A | * | 6/1981 | Bacal ............. A61B 17/025 29/268 |
| 5,616,143 A | * | 4/1997 | Schlapfer ........ A61B 17/7032 606/205 |
| 8,123,749 B2 | | 2/2012 | Serhan et al. |

(Continued)

OTHER PUBLICATIONS

Betz, et al., "An Innovative Technique of Vertebral Body Stapling for the Treatment of Patients with Adolescent Idiopathic Scoliosis: A Feasibility, Safety, and Utility Study" *Spine*, Lippincott Williams & Wilkins, Inc., Oct. 15, 2003: vol. 28, Issue 20S, p. S256, paragraphs 2, 11; S257, paragraph 1; p. S259, paragraph 2; p. S262, paragraph 1 http://www.vertebralstapling.com/uploads/00007632-200310151-00023.pdf.

(Continued)

*Primary Examiner* — Nicholas J Plionis
*Assistant Examiner* — Steven J Cotroneo
(74) *Attorney, Agent, or Firm* — Baker Botts L.L.P.

(57) ABSTRACT

Method for performing spinal correction surgery. The method includes creating at least one access opening in a patient, and implanting a plurality of anchor devices through the at least one access opening onto a plurality of corresponding vertebral bodies. Each anchor device has a channel defined therein. The method further includes disposing a tether into the channel of each of the plurality of anchor devices. A first end portion of the tether is secured to a first of the plurality of anchor devices. Additionally, the method includes translating the vertebral body corresponding to the selected anchor device using a pusher tool. Furthermore, the method includes applying a tension to the tether using a tensioner.

19 Claims, 39 Drawing Sheets

(56) References Cited

U.S. PATENT DOCUMENTS

| | | | |
|---|---|---|---|
| 2003/0073998 A1* | 4/2003 | Pagliuca | A61B 17/0218 606/86 A |
| 2004/0024411 A1 | 2/2004 | Newton et al. | |
| 2004/0138662 A1* | 7/2004 | Landry | A61B 17/1604 606/86 A |
| 2005/0010220 A1* | 1/2005 | Casutt | A61B 17/7008 606/86 A |
| 2005/0090899 A1* | 4/2005 | DiPoto | A61B 17/32002 623/17.11 |
| 2005/0131421 A1* | 6/2005 | Anderson | A61B 17/00234 606/99 |
| 2005/0131422 A1* | 6/2005 | Anderson | A61B 17/7079 606/104 |
| 2005/0203511 A1* | 9/2005 | Wilson-MacDonald | A61B 17/7044 606/254 |
| 2006/0009777 A1* | 1/2006 | Lim | A61B 17/025 606/90 |
| 2006/0036255 A1* | 2/2006 | Pond, Jr. | A61B 17/7079 606/86 R |
| 2007/0233075 A1* | 10/2007 | Dawson | A61B 17/7008 606/86 A |
| 2007/0299443 A1* | 12/2007 | DiPoto | A61B 17/02 606/86 A |
| 2008/0009863 A1* | 1/2008 | Bond | A61B 17/025 606/86 A |
| 2008/0114403 A1* | 5/2008 | Kuester | A61B 17/7037 606/308 |
| 2008/0140122 A1 | 6/2008 | Bethell | |
| 2008/0140133 A1* | 6/2008 | Allard | A61B 17/7022 606/308 |
| 2008/0249531 A1* | 10/2008 | Patterson | A61B 17/7089 606/99 |
| 2009/0054902 A1 | 2/2009 | Mickiewicz et al. | |
| 2009/0198281 A1* | 8/2009 | Rice | A61B 17/7031 606/279 |
| 2009/0248077 A1* | 10/2009 | Johns | A61B 17/7011 606/246 |
| 2009/0259262 A1* | 10/2009 | Nayet | A61B 17/7079 606/86 A |
| 2009/0281575 A1 | 11/2009 | Carls et al. | |
| 2010/0042149 A1* | 2/2010 | Chao | A61B 17/7077 606/246 |

OTHER PUBLICATIONS

International Search Report dated Aug. 11, 2014 in International Application No. PCT/US14/28016.
Supplementary European Search Report dated Oct. 26, 2016 in EP Application No. EP 14763561.

* cited by examiner

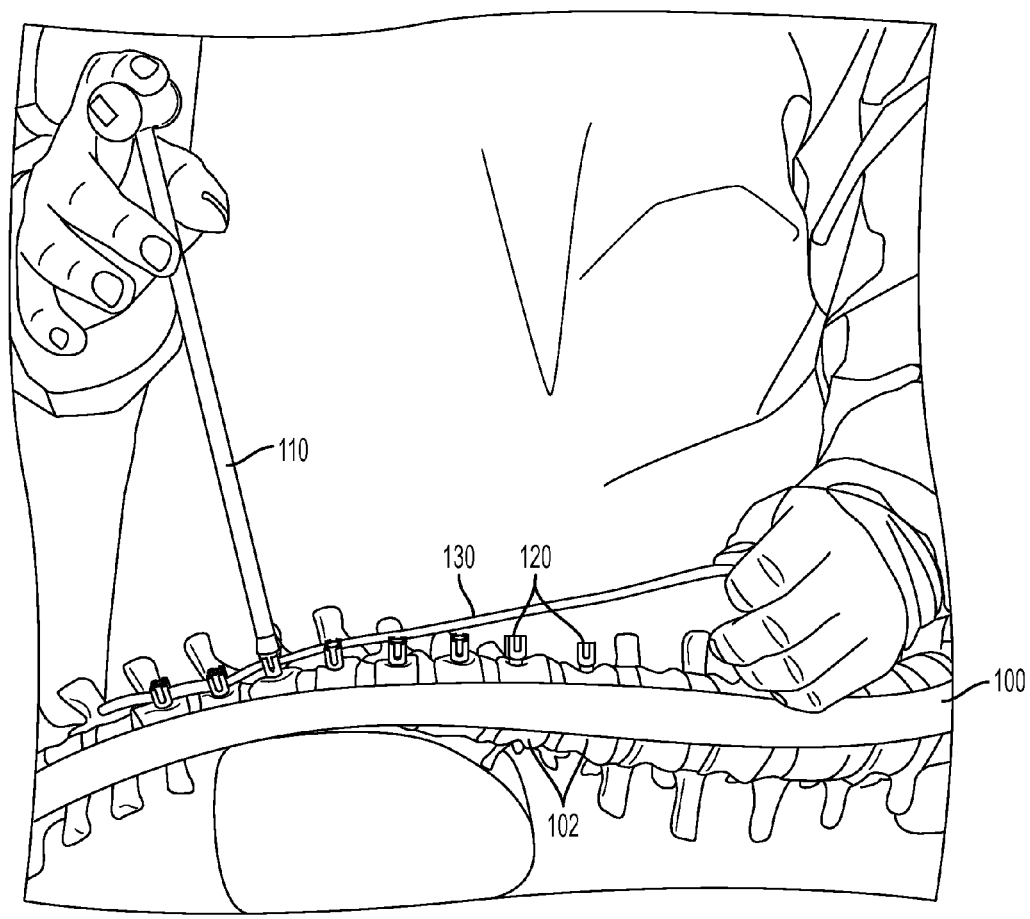
FIG. 1B1

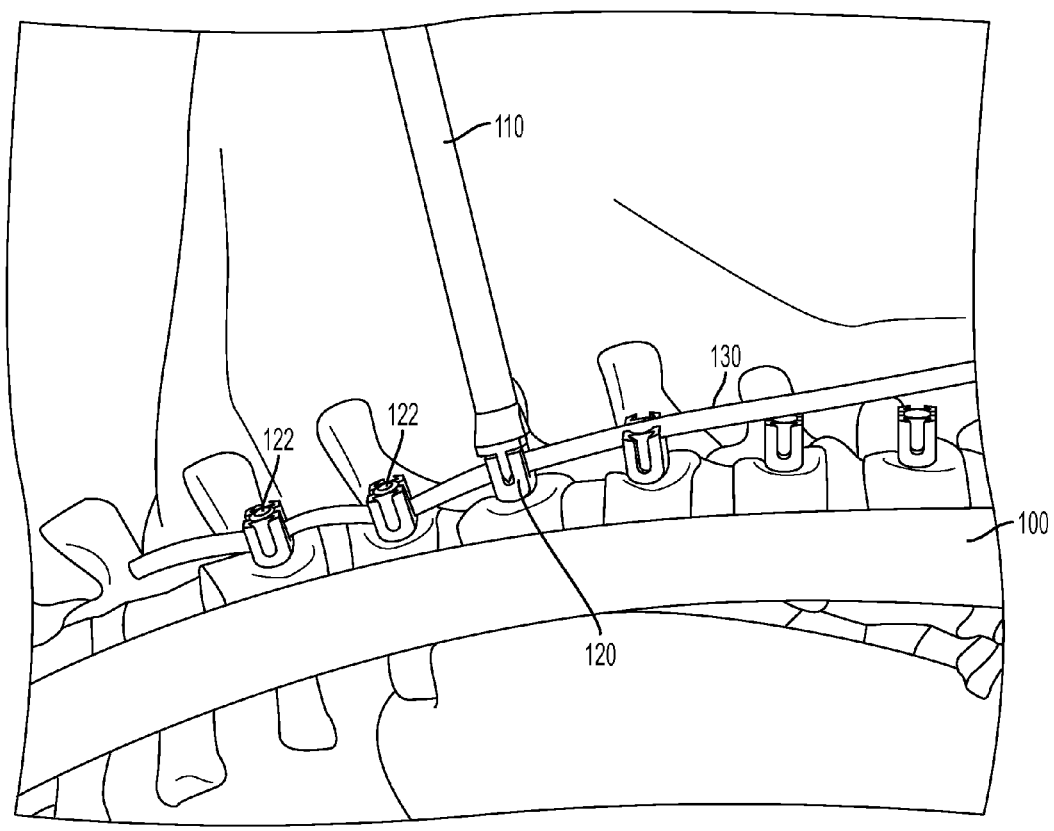
FIG. 1B2

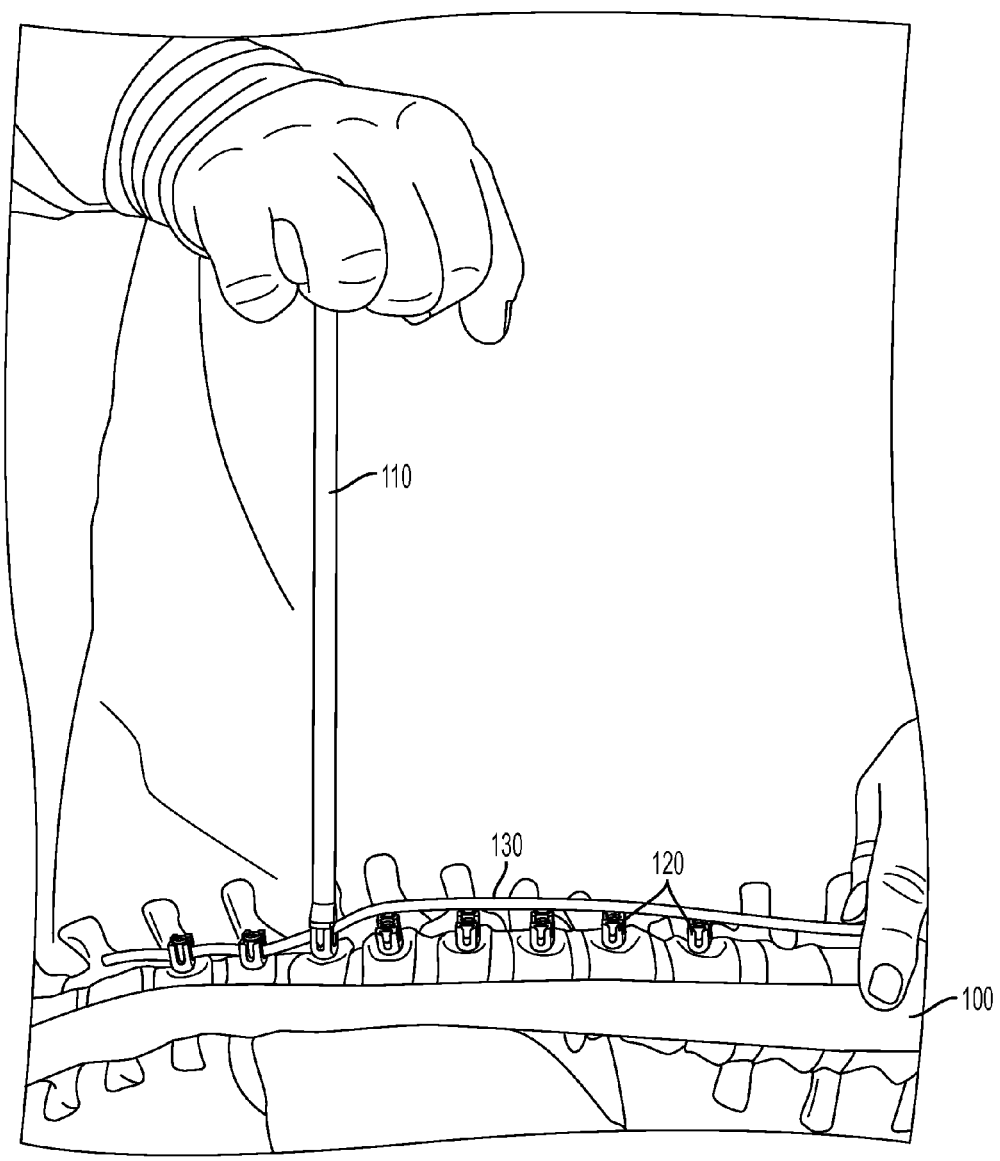
FIG. 1C1

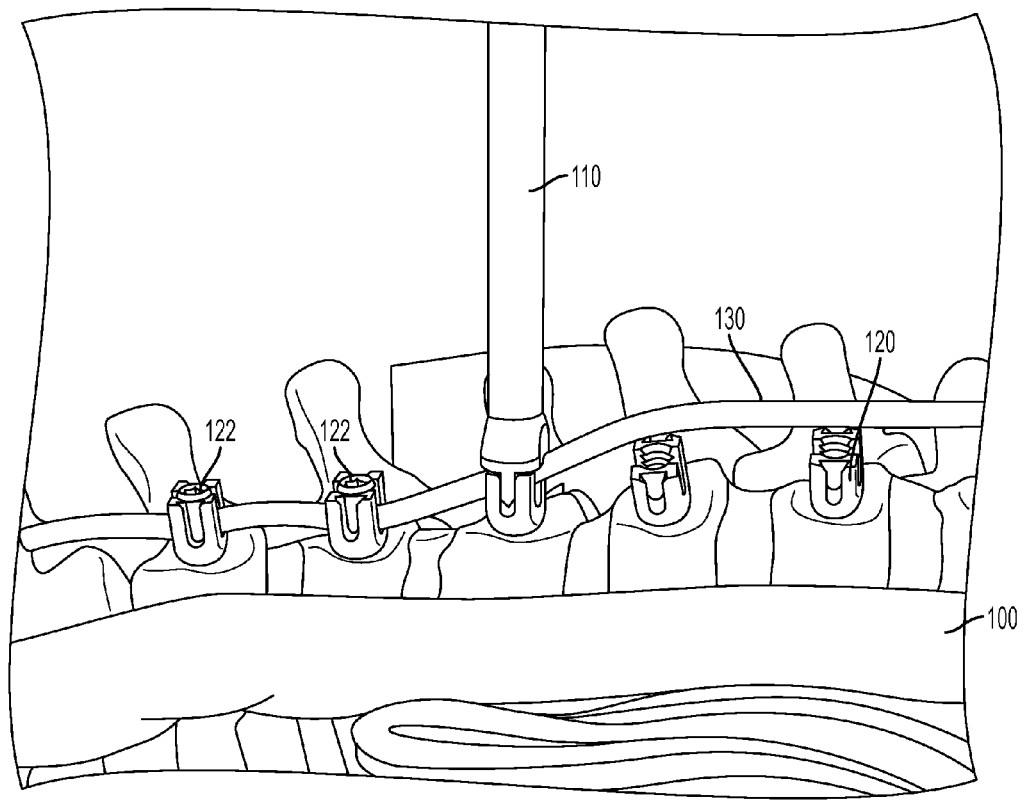
FIG. 1C2

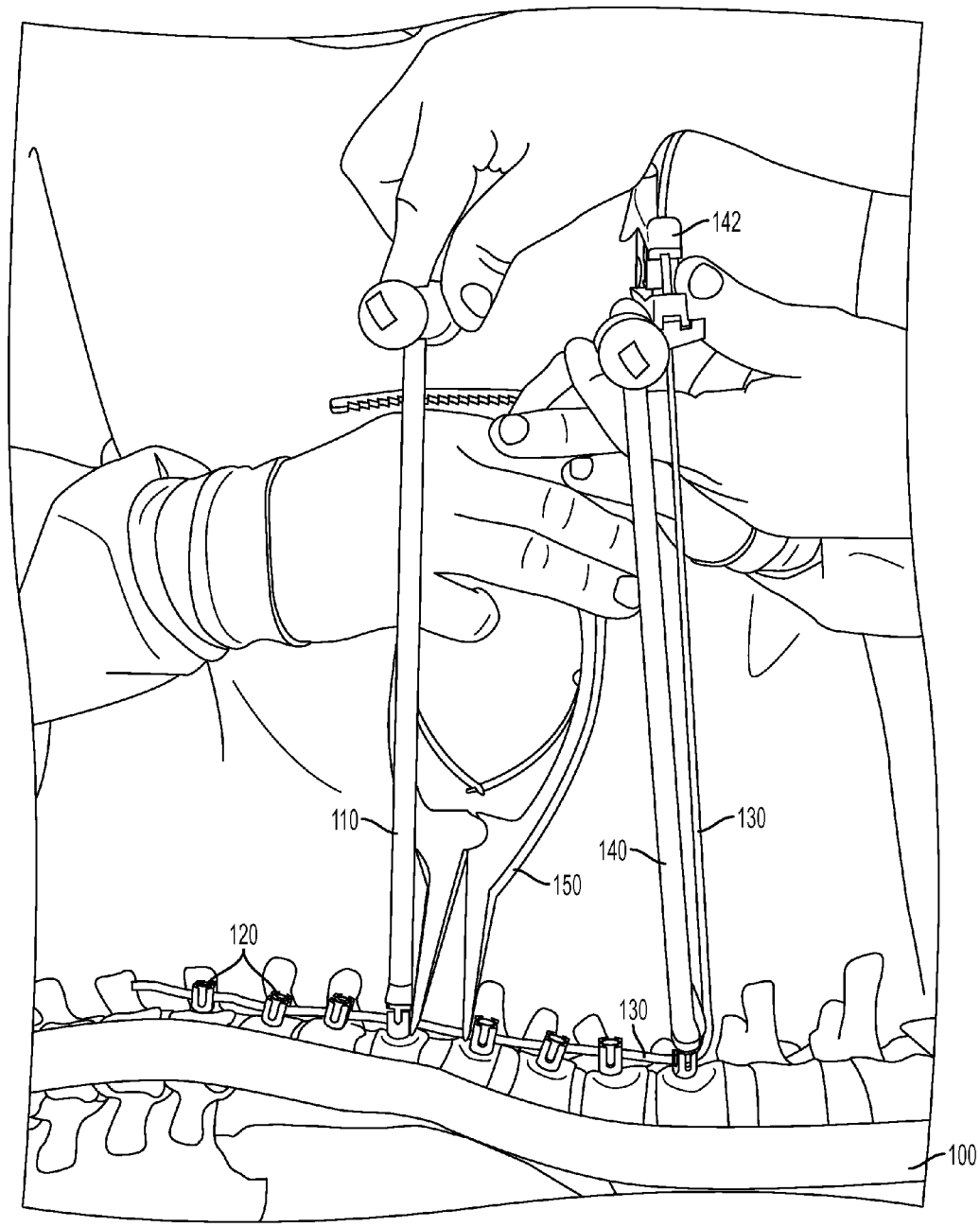
FIG. 3C1

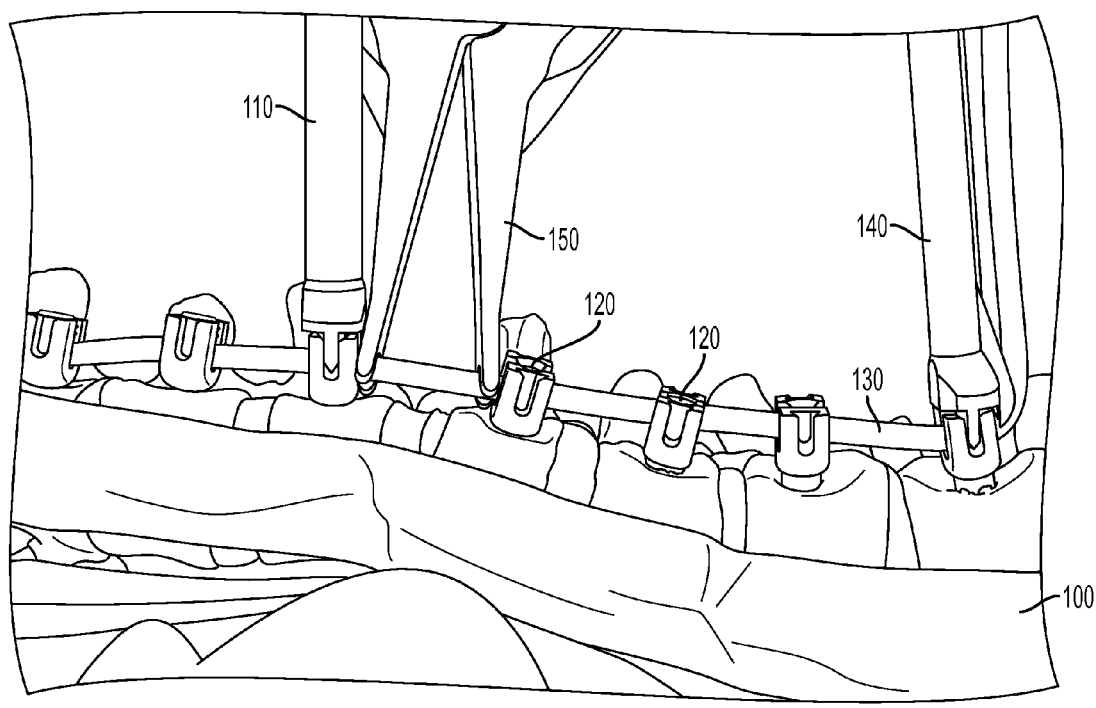
FIG. 3C2

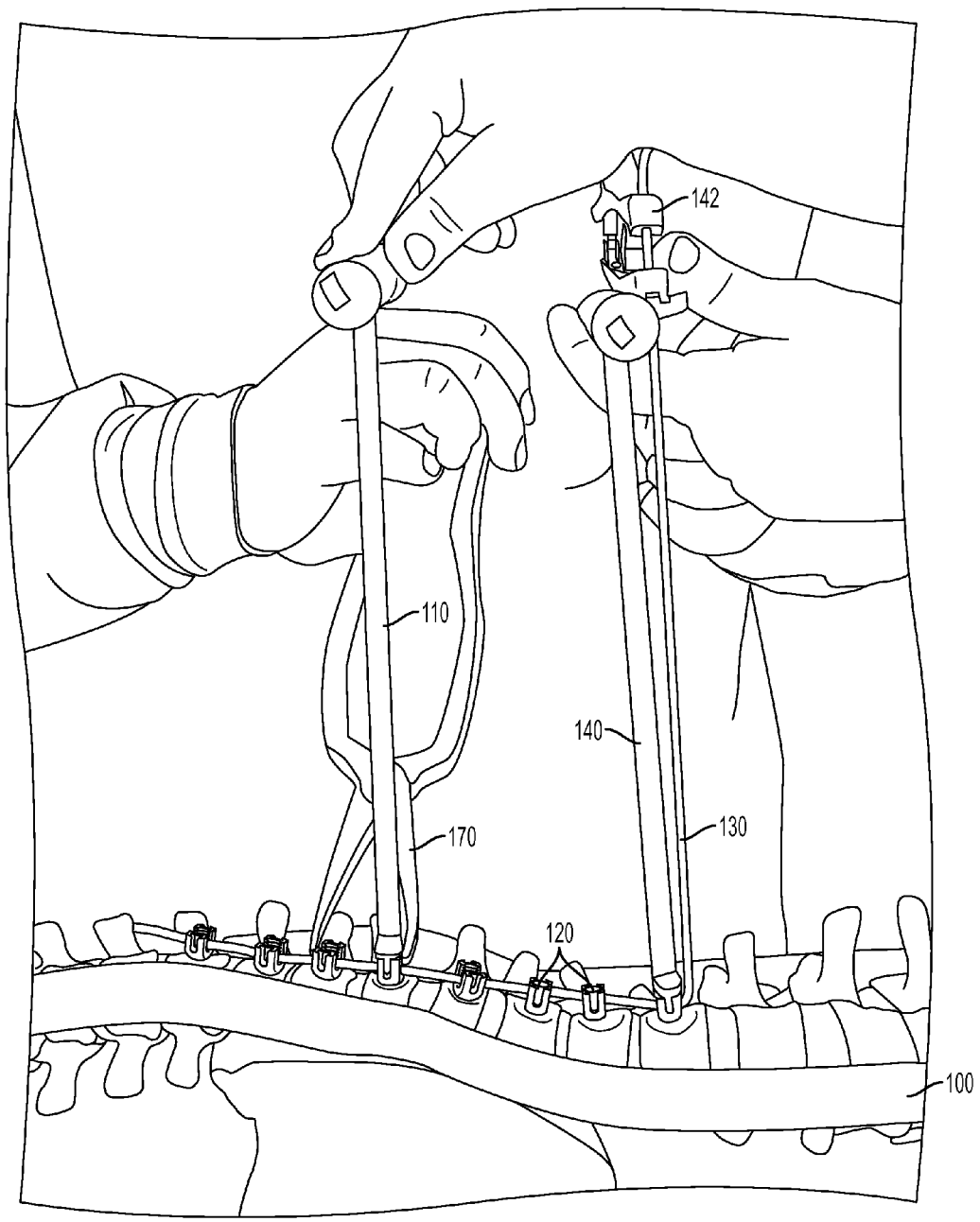
FIG. 3D1

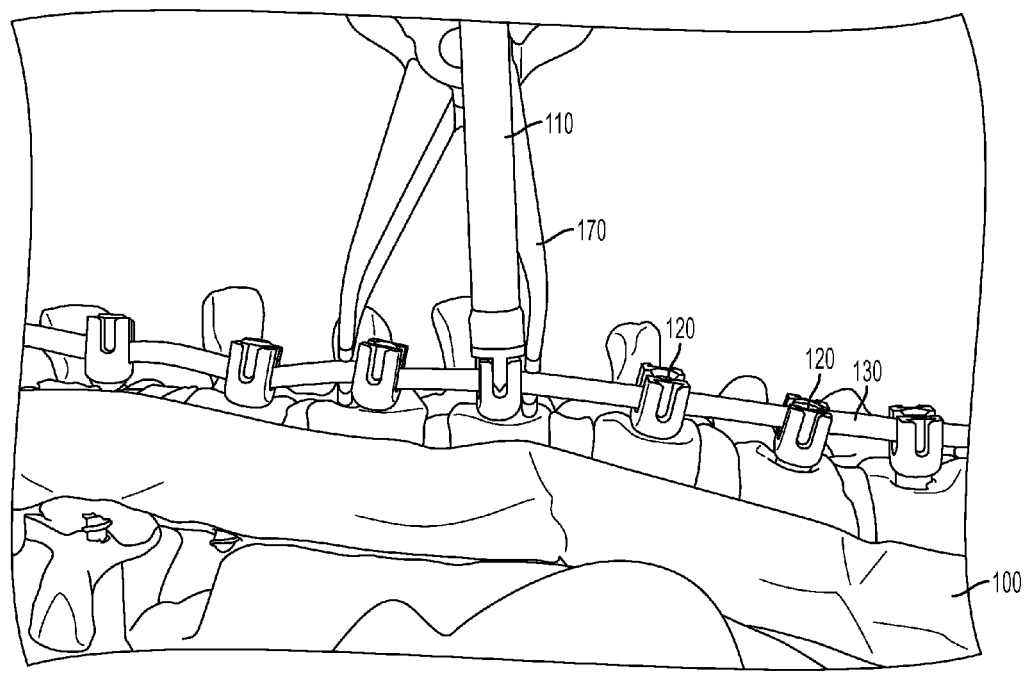
FIG. 3D2

METHODS AND TECHNIQUES FOR SPINAL SURGERY

CROSS-REFERENCE TO RELATED APPLICATIONS

This application is a continuation of International Patent Application No. PCT/US2014/028016 filed, Mar. 14, 2014, and claims priority to U.S. Provisional Application Ser. No. 61/791,982, filed Mar. 15, 2013, to both of which priority is claimed and the contents of both of which are incorporated herein in their entireties.

BACKGROUND

Certain motion sparing techniques for the treatment of idiopathic scoliosis (IS) can be one alternative to conventional bracing and spinal fusion. The use of bracing in the treatment of idiopathic scoliosis can be ineffective. For example, psychosocial elements surrounding brace-wear can exist, and bracing can be ineffective to halt curve progression. Adverse effects of spinal fusion, including inhibition of growth over the length of the construct as well the potential for adjacent level disc degeneration, can occur. Additionally, truncal range of motion, spinal mobility, and/or muscle endurance can potentially be limited by spinal fusion.

Alternative surgical systems can include growing rods, the Vertical Expandable Prosthetic Titanium Rib (VEPTR), and vertebral body stapling (VBS). In addition, anterior vertebral body tethering (AVBT) can be utilized as an alternative to both spinal fusion and the fusionless techniques described above. However, there remains a need for improved surgical approaches to halt curve progression while permitting growth of the spine.

SUMMARY

The purpose and advantages of the disclosed subject matter will be set forth in and apparent from the description that follows, as well as learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a method for performing spinal correction surgery. The method includes creating at least one access opening in a patient, and implanting a plurality of anchor devices through the at least one access opening onto a plurality of corresponding vertebral bodies. Each anchor device has a channel defined therein. The method further includes disposing a tether into the channel of each of the plurality of anchor devices. A first end portion of the tether is secured to a first of the plurality of anchor devices. Additionally, the method includes translating the vertebral body corresponding to the selected anchor device using a pusher tool. Furthermore, the method includes applying a tension to the tether using a tensioner.

Further in accordance with the disclosed subject matter, at least one access opening can be a portal, or a plurality of portals. For example, the portal can be a thoracoscopic portal.

In accordance with another aspect of the invention, the anchor devices can be spine screws or the like, that include a threaded shank portion and a head portion, wherein the channel is disposed proximate the head portion. The spine screws can include a fastener to secure the tether within the channel. The tether can be made of polyethylene-terephthalate (PET) or any other suitable material. Translating the corresponding vertebral body and applying the tension to the tether can be performed simultaneously to produce a corrective force for proper positioning of the selected vertebral body.

In accordance with another aspect of the disclosed subject matter, a compressive and/or distractive force can be applied to an adjacent vertebral body, to adjust the relative position of the two vertebral bodies. The compressive and/or distractive forces can be applied simultaneously or sequentially to the translating the selected vertebral body. Once the corresponding vertebral body is properly positioned, the tether can be secured to the selected anchor device using the fastener.

Furthermore, subsequent anchor devices (e.g. a second selected anchor device) can be engaged for translation of the corresponding vertebral body while applying tension to the tether. Once each desired vertebral body is properly positioned, the second end portion of the tether can be secured to the last anchor device of the system. The tether can be cut to a length greater than the distance between the anchor devices, to allow for continued growth of the patient.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the methods and apparatus of the disclosed subject matter. Together with the description, the drawings serve to explain the principles of the disclosed subject matter.

BRIEF DESCRIPTION OF THE DRAWINGS

FIG. 1B1 demonstrates for illustration a pre-translation technique on a spine model (e.g., a sawbone from Pacific Research Laboratories, Inc., Vashon, Wash., USA) in accordance with the disclosed subject matter.

FIG. 1B2 is an enlarged view of FIG. 1B1.

FIG. 1C1 demonstrates translation using a thoracoscopic vertebral body pusher on a sawbone in accordance with the disclosed subject matter.

FIG. 1C2 is an enlarged view of FIG. 1C1.

FIG. 3C1 demonstrates open distraction on sawbone in accordance with the disclosed subject matter.

FIG. 3C2 is an enlarged view of FIG. 3C1.

FIG. 3D1 demonstrates open compression on sawbone in accordance with the disclosed subject matter.

FIG. 3D2 is an enlarged view of FIG. 3D1.

DETAILED DESCRIPTION OF THE PREFERRED EMBODIMENT

Figure 1A:
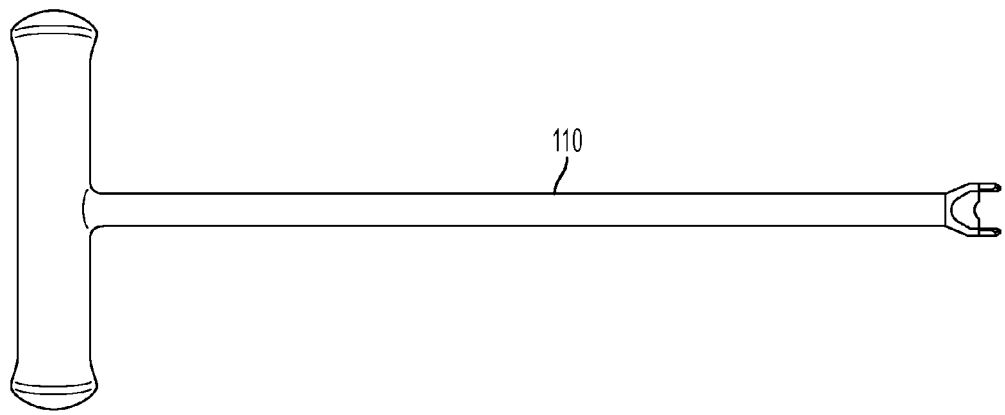
FIG. 1A is an image of a thoracoscopic vertebral body pusher used in accordance with the disclosed subject matter.
Figure 1D:
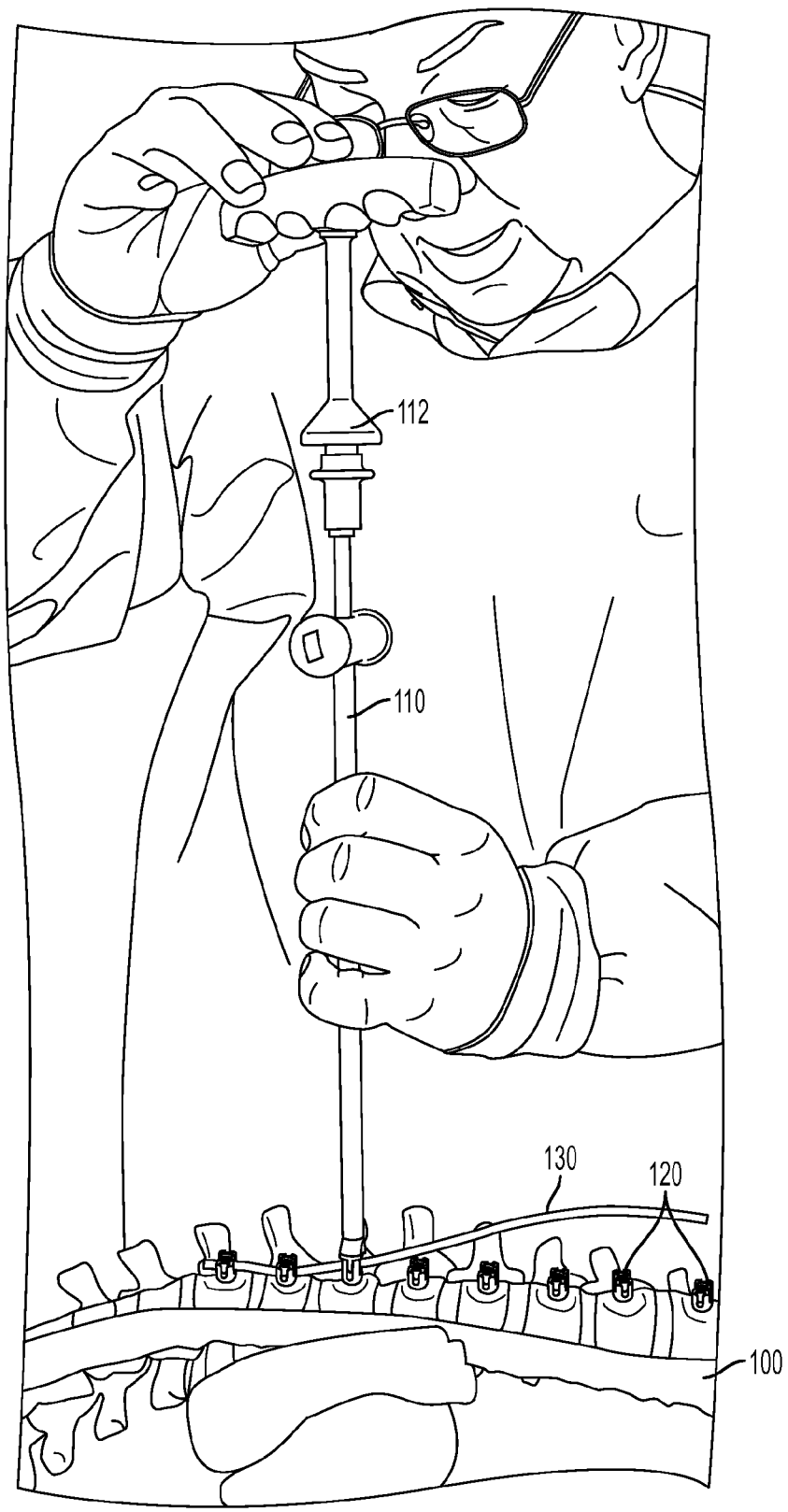
FIG. 1D demonstrates translation using a thoracoscopic vertebral body pusher with insertion of a set screw in the anchor device on a sawbone in accordance with the disclosed subject matter.

The methods presented herein can be used for treating and correcting spinal deformities in patients. The disclosed subject matter is particularly suited for surgery to correct spinal deformities due to scoliosis or similar ailments.

As such, and in accordance with the disclosed subject matter, a method is provided for performing spinal correction surgery. The method includes creating at least one access opening in a patient and implanting a plurality of anchor devices through the at least one access opening onto a plurality of corresponding vertebral bodies. Each anchor device has a channel defined therein. The method further includes disposing a tether into the channel of each of the plurality of anchor devices. A first end portion of the tether is secured to a first of the plurality of anchor devices. Additionally, the method includes translating the vertebral body corresponding to the selected anchor device using the pusher tool. Furthermore, the method includes applying a tension to the tether using a tensioner.

For purpose of illustration and not limitation, reference will now be made in detail to the various exemplary embodiments of the disclosed subject matter, exemplary embodiments of which are illustrated in the accompanying drawings. The structure and corresponding method of operation of the disclosed subject matter will be described in conjunction with the detailed description of the system.

The accompanying figures serve to further illustrate various embodiments and to explain various principles and advantages in accordance with the disclosed subject matter. Generally, the method and additional options are depicted substantially in the flow chart of FIG. 10. For purpose of explanation and illustration, and not limitation, exemplary embodiments of the method and related tools in accordance with the disclosed subject matter are shown in FIGS. 1-9 as applied to a spine model (e.g. a sawbone). However, it is understood the described method can be used with a variety of techniques and indications, including minimally invasive techniques. Furthermore, it is understood that reference to the location of the target sites and to the specific brand or make of instruments and implants is for purpose of illustration only, and not limitation.

According to the presently disclosed subject matter, an exemplary technique for spinal correction surgery 200 is provided. The patient is placed on the operating table in the lateral decubitus position with the right side up and is appropriately secured. The patient undergoes the standard preparation and drape. For example, at 210, two small (for example, 5-mm) thoracoscopic portals are placed in the anterior axillary line around T6 and T8. An additional 5-mm portal can be placed around T10 if additional retraction is needed. A thoracoscopic camera is inserted through one of the portals and CO2 insufflation utilized. A scalpel, such as a Harmonic scalpel, is inserted through another portal, and levels are confirmed with fluoroscopy.

Utilizing the Harmonic scalpel, the pleura is dissected off the anterolateral aspect of the vertebral body and reflected to visualize the rib head. The segmental vessels are sacrificed at every level using the Harmonic scalpel, with ligature staples used if necessary. Additionally or alternatively, smaller or modified staples can be used without sacrificing the segmental vessels. Care is taken to ensure that the disc space is not violated. Once the exposure has been completed, at 220, the vertebral anchor devices 120 are placed.

A 3-cm incision can be made in the posterior axillary line around the T6/7 interspace. The location of this incision can be determined by first injecting saline through a syringe/needle to ensure optimal access/angulation for screw placement. The muscles can be dissected using the Bovie bipolar electrocautery device and undermined to provide maximal access.

A 15-mm portal is inserted and, under direct visualization, a vertebral body staple is placed just anterior to the rib head. The positioning of the staple is confirmed with an AP fluoroscopy image. Once optimized, the staple is malleted into place. Alternatively, the technique can be performed without placing a vertebral body staple, and the anchor devices 120, embodied herein as vertebral body screws, can be placed as described herein below.

A tap is introduced into the staple hole and directed toward the contralateral pedicle on the AP fluoroscopy image. The sagittal orientation is confirmed by making a second working incision around the T9/10 interspace, introducing a second 15-mm portal, and placing the camera through that portal to more accurately assess the sagittal angulation. The target is the contralateral rib head. Care is taken not to breach the spinal canal. Alternatively, the technique can be performed without the tap, and the anchor devices 120, embodied herein as a vertebral body screw, can be inserted directly.

The tap is progressively advanced until 1-2 threads are emerging out of the contralateral side of the vertebral body. At this point, the length of the anchor device 120 is determined. The tap is removed and any bony bleeding stopped with a hemostatic agent. In some embodiments, the technique can be performed without bicortical purchase, for example by inserting the tap and/or the screw a shorter distance. The anchor device 120 is placed again under direct AP fluoroscopic guidance.

For example and without limitation, the anchor device 120 can be chosen as an appropriate-size Zimmer Dynesys 6.0 millimeter screw, which can be advanced by hand. Bicortical purchase is confirmed. If a thoracotomy is performed, the screw on the contralateral side can be palpatated to confirm bicortical fixation.

Additionally, it should be confirmed that there is no excessive prominence of the screw tip on the contralateral side of the vertebral body 100, or any significant impingement on the aorta (if it is a right-sided approach).

The steps of placement of the screw or similar anchor device 120 are repeated for each vertebral body segment 102 as required or desired.

An inferior 3-cm thoracoscopic portal incision over the T9-T10 interspace in the posterior axillary line is made to assist in placing the bottom anchor devices 120. Additionally, a larger distal incision of 5 cm or greater and/or thoracotomy can be provided to better facilitate visualization and application of the corrective forces. 15-mm portals are placed into each-of the three incisions in the posterior axillary line. In addition, three 5-mm portals are placed through the portals in the anterior axillary line. It is understood that alternative access openings can be used as desired or appropriate.

In accordance with the disclosed method, at 230, a tether 130, such as a PET web, is introduced from the inferior most 15-mm portal. However, it is recognized that the tether 130 can be introduced through any of the other portals. The tether 130 is grabbed with a thoracoscopic grasper which is introduced through a 5-mm anterior portal. The tether 130 is then placed within the channels of the anchor devices, e.g. the tulips of the anchor devices 120. At 240, a set screw or similar fastener 122 is introduced through the superior most 15-mm portal and tightened on the top most anchor device 120 to secure the first end of the tether 130 in the channel, in this instance T6, thereby securing the tether 130 to the anchor device 120.

At 250, a thoracoscopic vertebral body pusher 110 is introduced through the middle 15-mm portal, and at 260, used to apply a downward and anterior translational force to the next adjacent vertebral body segment 102 for coronal and axial correction of the spine 100 across the apex, as shown for illustration in FIGS. 1A-D. In accordance with the disclosed subject matter, the thoracoscopic vertebral body pusher 110 for use herein is configured to be longer than a normal body pusher, in order to extend through a thoracoscopic portal and still reach the spine 100. A longer set screw inserter 112, which can fit inside the pusher 110, complements the longer pusher 110 to accommodate the longer instrument.

As appropriate and as embodied herein, a modified multilevel vertebral body pusher 110 can be provided to grasp tulips of up to 3 anchor devices 120 simultaneously, to allow for maximal curve correction via translation over up to 3 vertebral segments. This allows a translational corrective force to be applied to correct the spinal curvature.

Figure 5:
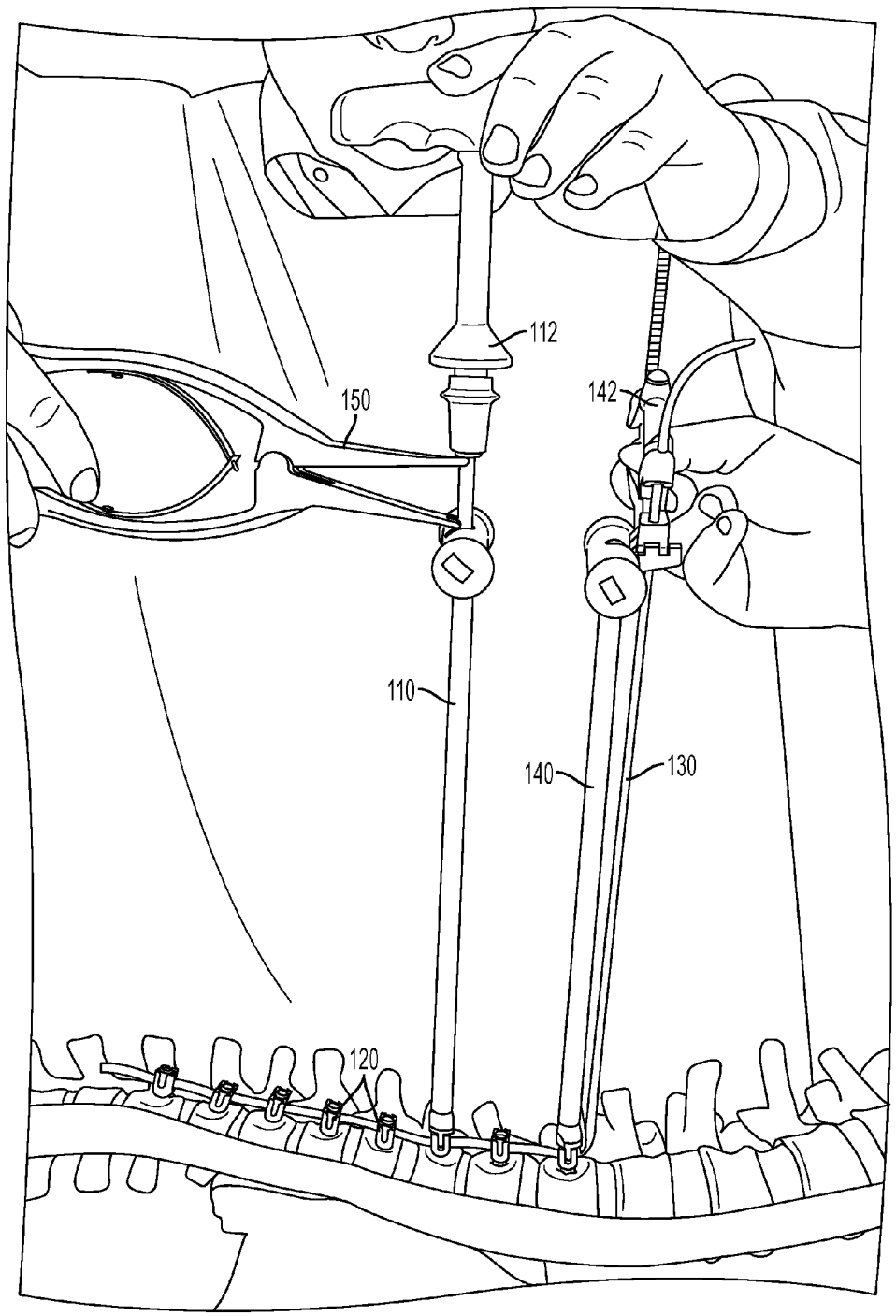
FIG. 5 demonstrates releasing a screw driver from a screw using distractor.
Figure 6A:
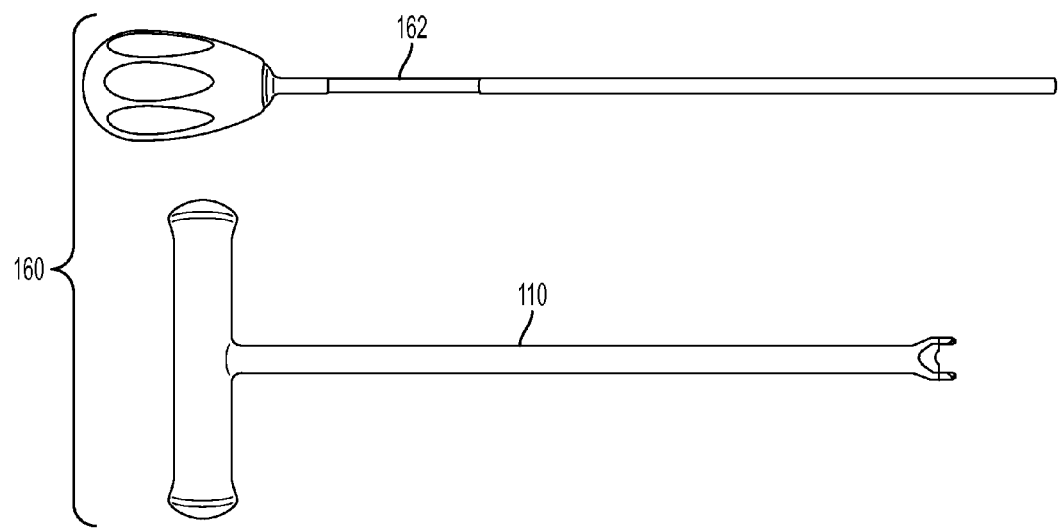
FIG. 6A is an image of a popper and pusher apart for use in accordance with the disclosed subject matter.
Figure 6B:
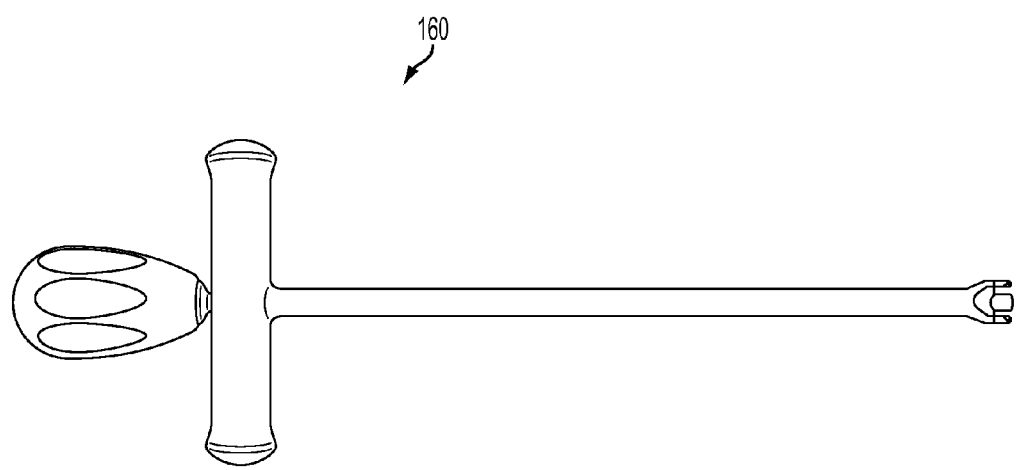
FIG. 6B is an image of the popper and pusher of FIG. 6A assembled together.
Figure 6C:
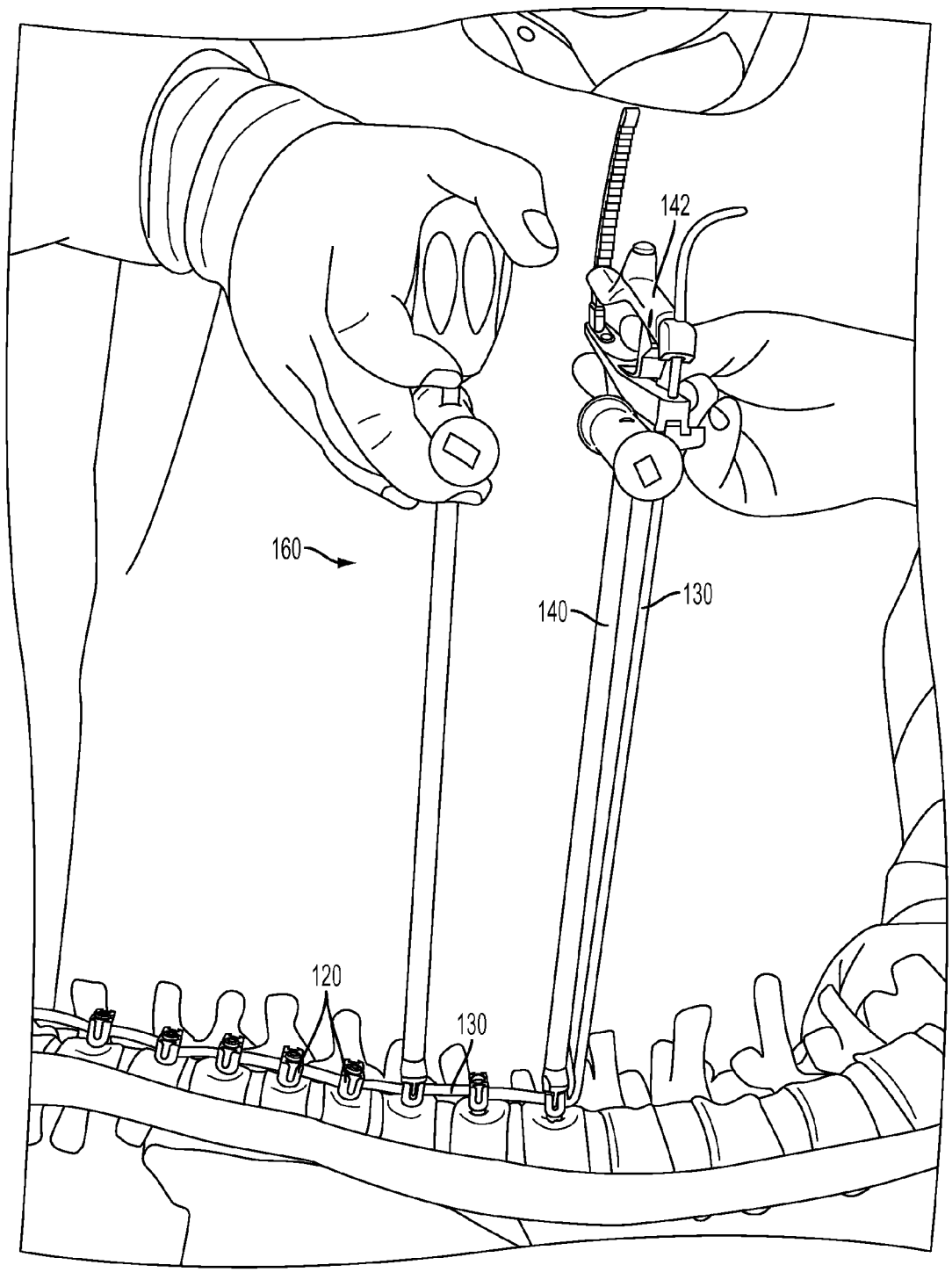
FIG. 6C demonstrates use of the popper on sawbone in accordance with the disclosed subject matter.
Figure 6D:
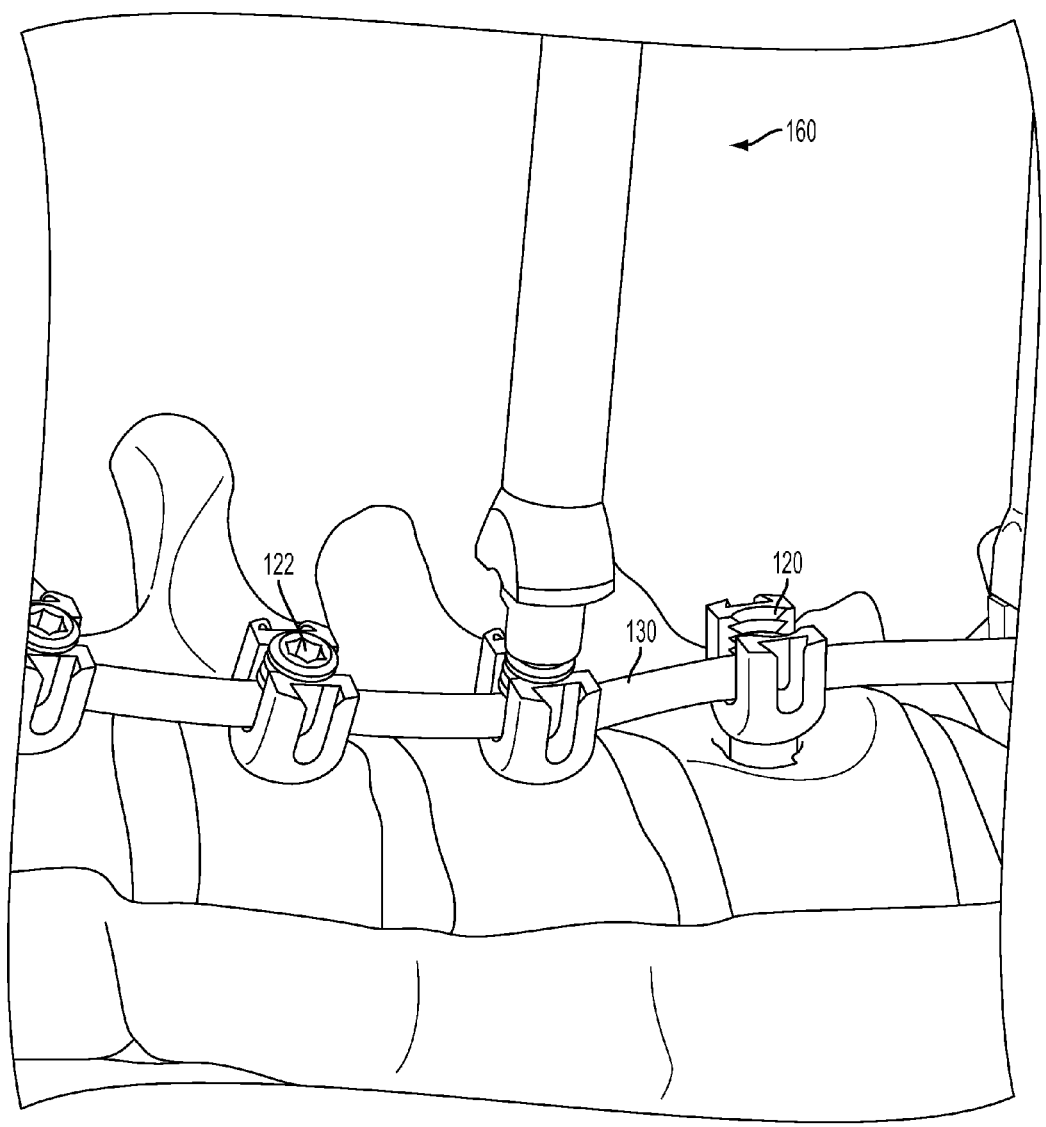
FIG. 6D demonstrates the pusher disengaged.

Excessive force and manipulation can weaken the screw bone interface. If it becomes difficult to remove the set screw driver 112 from the fastener 122, a distractor 150 as shown in FIG. 5 can be used to facilitate this removal. Dislodging the set screw driver 112 using a distractor can minimize the risk of weakening the screw-bone interface. Similarly, if removing the modified pusher 110 from the anchor device 120 becomes difficult, using a popper tool 160 as shown in FIGS. 6A-D can facilitate such removal.

Figure 2A:
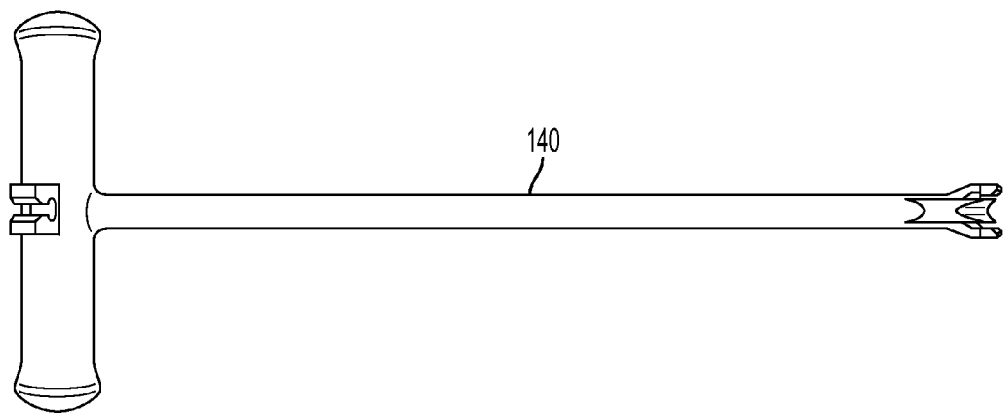
FIG. 2A is an image of a tensioning tower used in accordance with the disclosed subject matter.
Figure 2B:
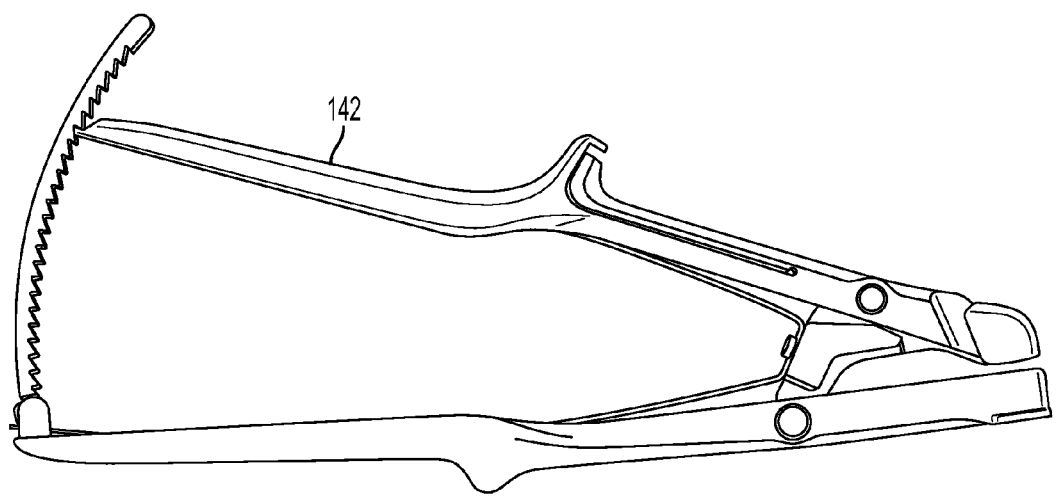
FIG. 2B is an image of a modifier tensor used in accordance with the disclosed subject matter.
Figure 2C:
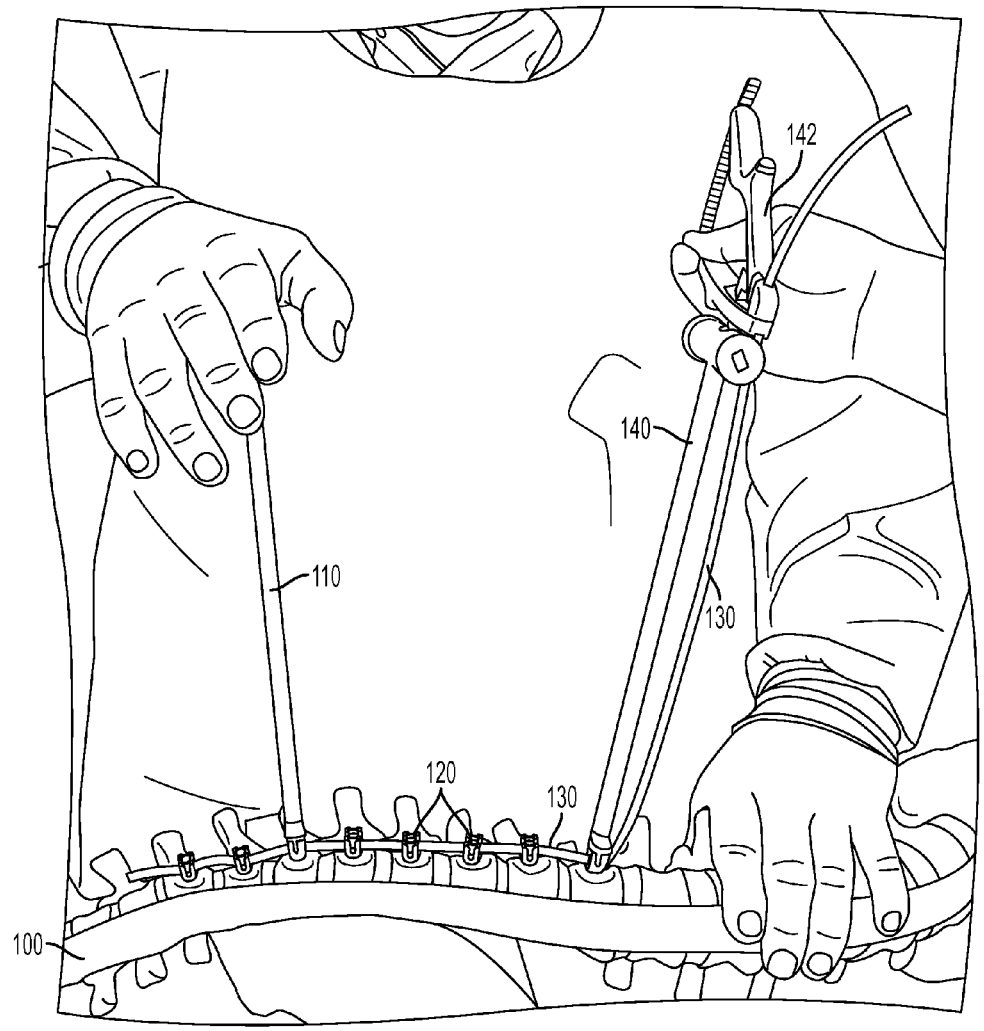
FIG. 2C demonstrates translation and tensioning on a sawbone pre correction in accordance with the disclosed subject matter.
Figure 2D:
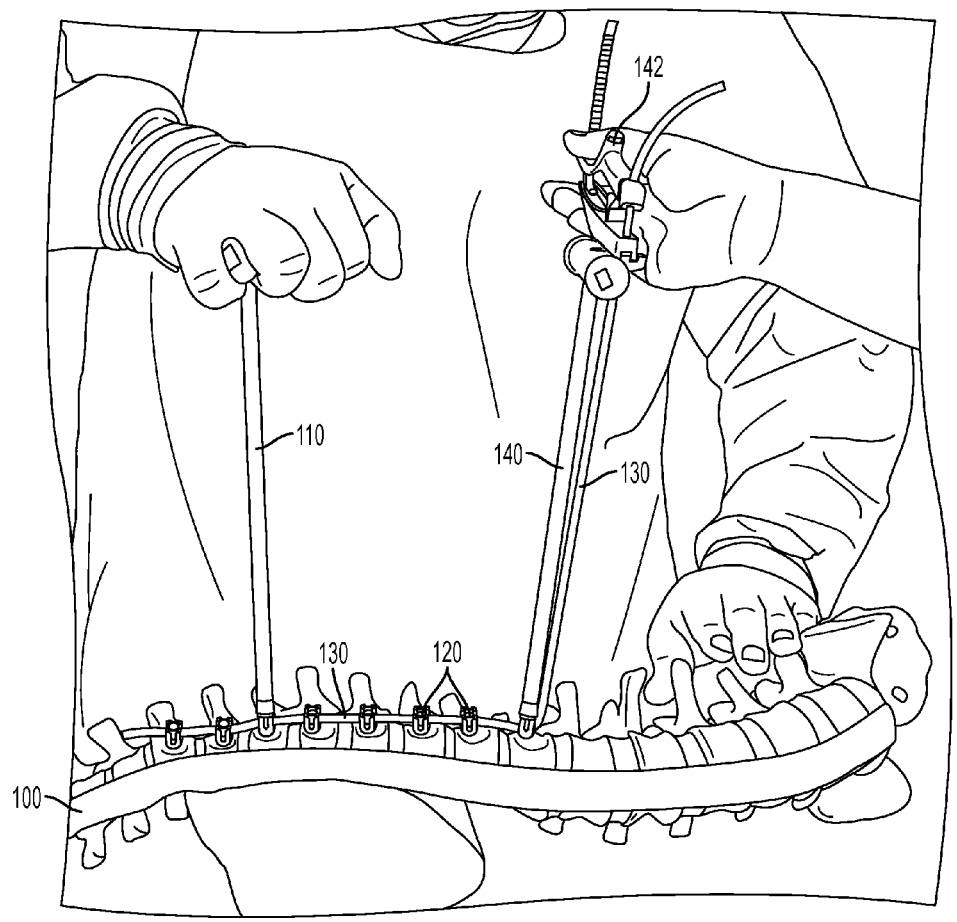
FIG. 2D demonstrates translation and tensioning on sawbone post correction in accordance with the disclosed subject matter.
Figure 2E:
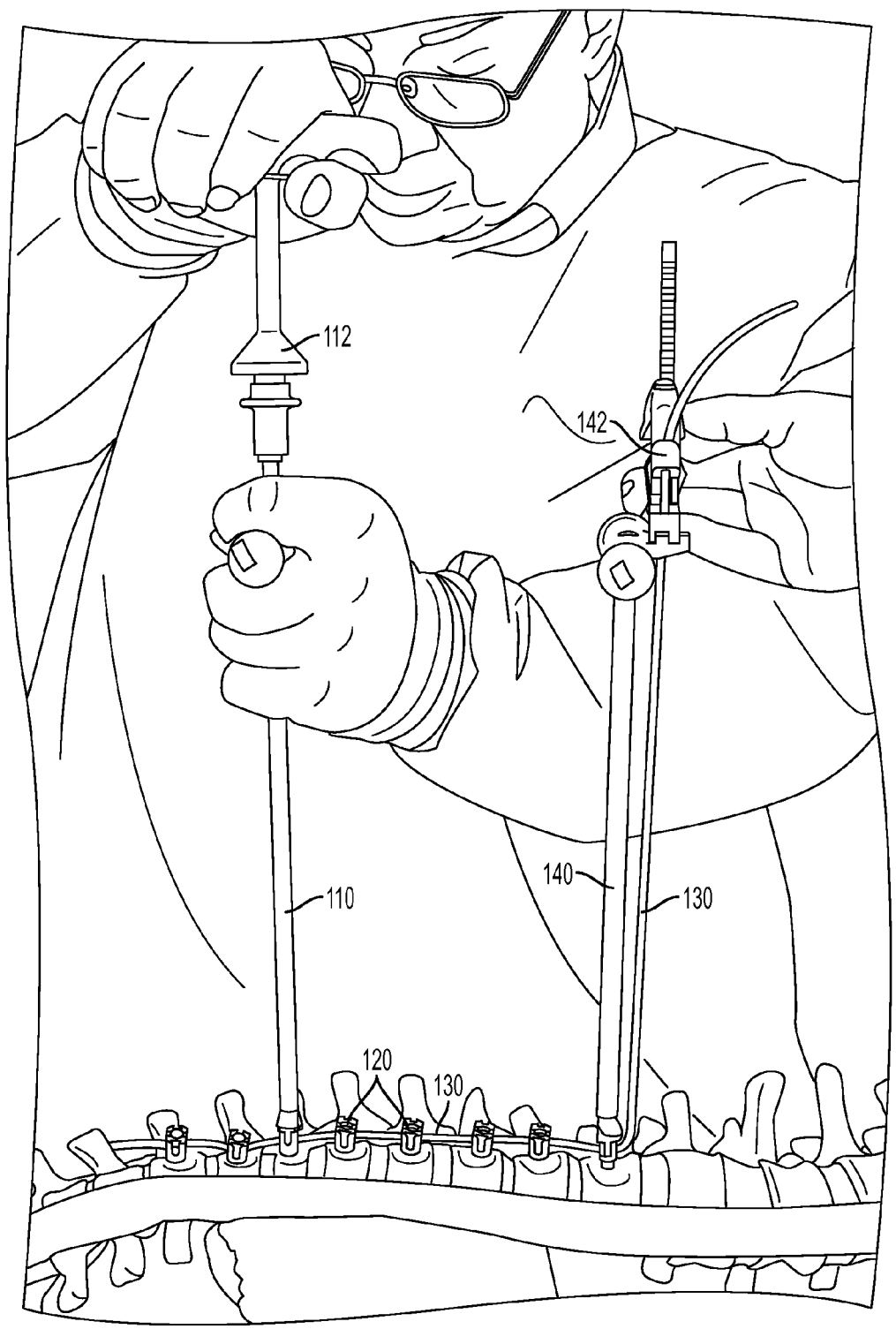
FIG. 2E demonstrates translation and tensioning on a sawbone post correction with insertion of a set screw in the anchor device in accordance with the disclosed subject matter.

Further in accordance with the disclosed subject matter, a pusher 110 is then introduced through the top most 15-mm portal and engaged with the second anchor device 120 from the top (for example, T7). At 270, as depicted in FIGS. 2A-B, a tensioner tower 140 is placed at an inferior anchor device 120, such as the next to last distal anchor device 120, so as not to stress the most distal fixation point in the construct (in this instance, T12). However, it will be recognized that the tensioner 140 can be placed at a more proximal screw. A modified tensioner 142 is then applied to the tensioner tower 140, in order to apply tension to a second end of the tether 130. In this manner, any slack in the tether 130 between vertebral body segments 102 is removed by tensioning. Furthermore, in some embodiments, the tensioner 142 can include a self-locking feature. For example, the tensioner 142 can be modified to include a locking cylinder through which the tether 130 can be fed and locked by pressing a button to engage a lock, such as a latching or abutting engagement.

Simultaneously, or sequentially with the translational force of the pusher 110, the tensioner 142 (such as depicted in FIGS. 2A-B) is maximally engaged on T11 to apply compressive forces across the convexity of the scoliotic curve in order to obtain 3-dimensional curve correction, as shown in FIGS. 2C-F.

Figure 2F:
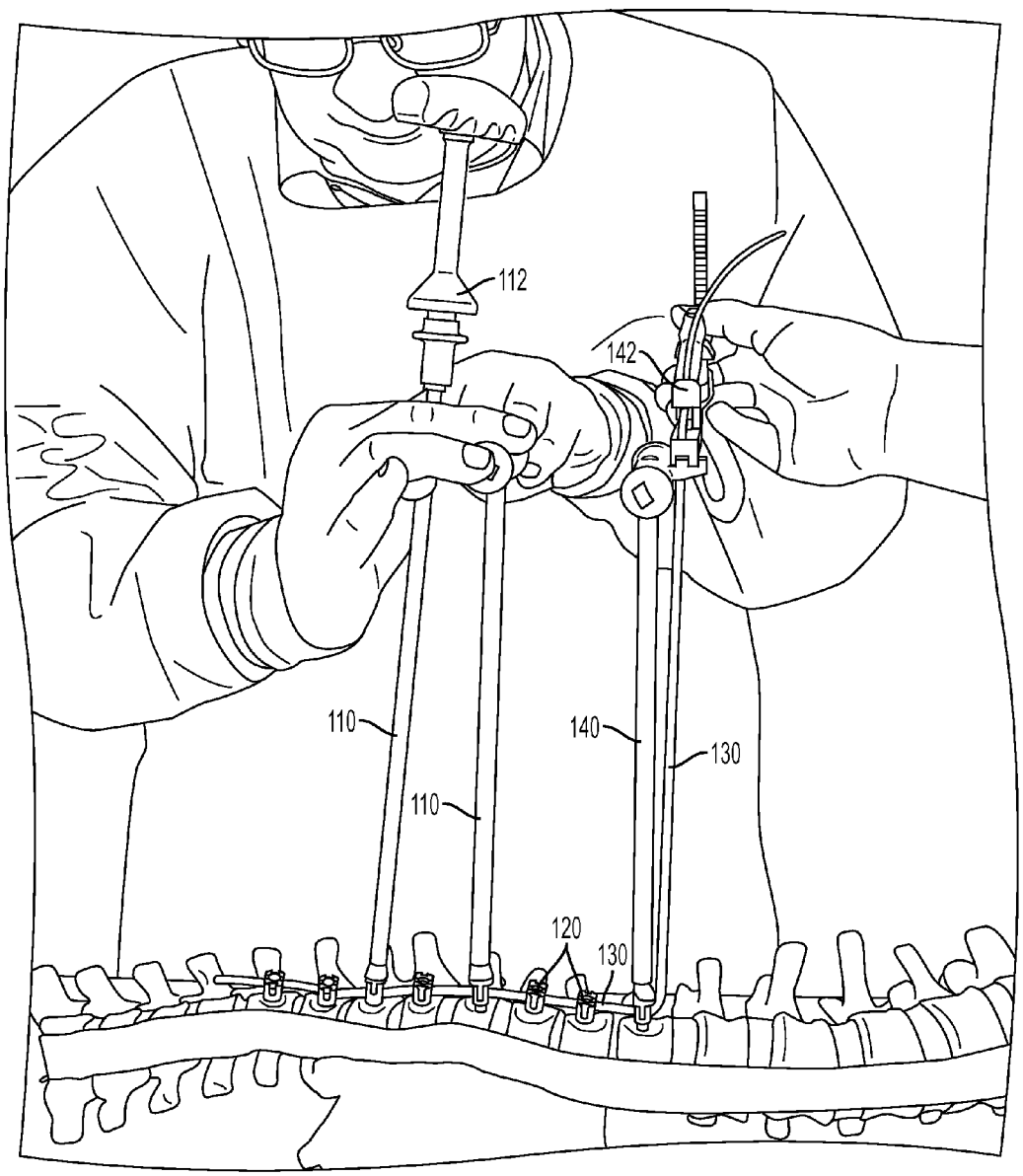
FIG. 2F demonstrates double translation and tensioning on sawbone in accordance with the disclosed subject matter.
Figure 3A:
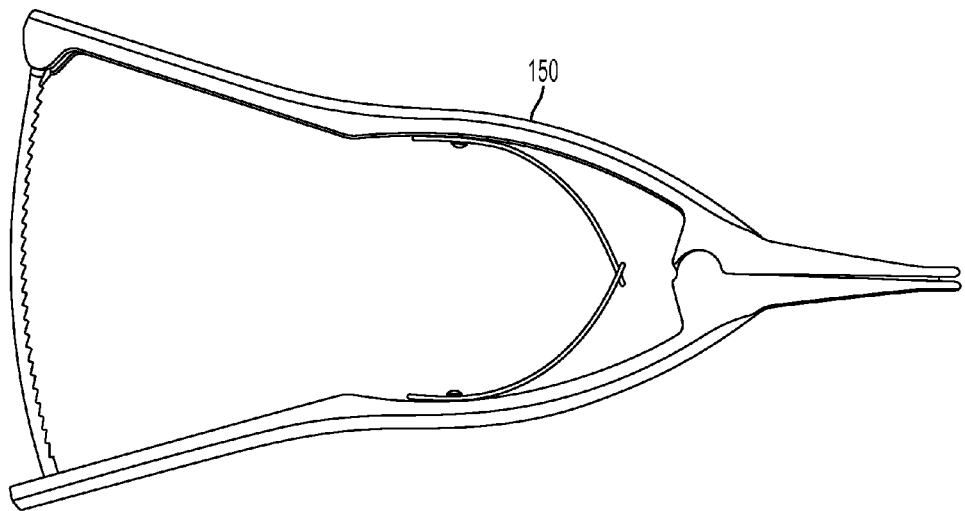
FIG. 3A is an image of an open distractor used in accordance with the disclosed subject matter.
Figure 3B:
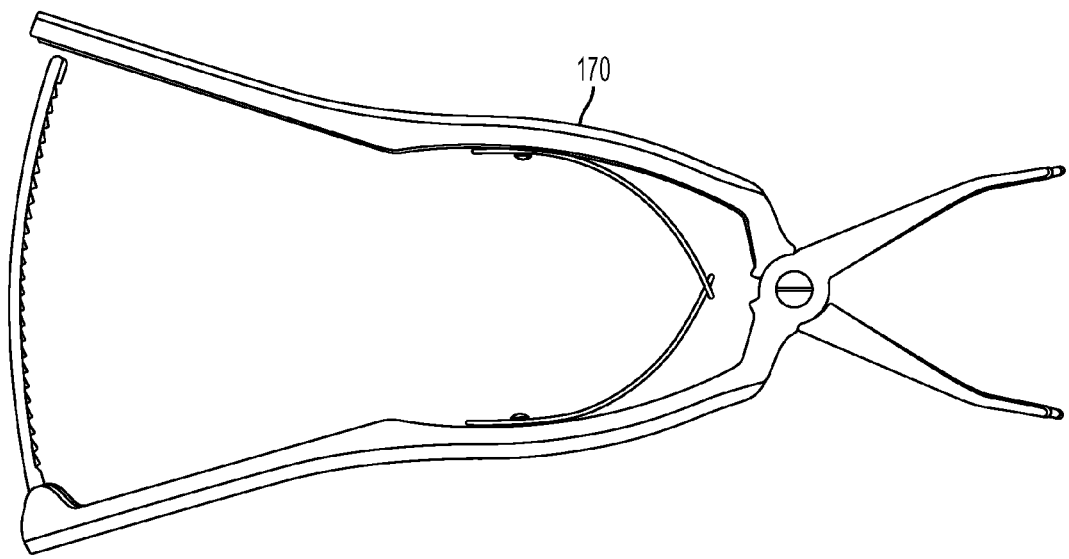
FIG. 3B is an image of an open compressor used in accordance with the disclosed subject matter.

After the corrective forces are generated and applied by the combination of translation and tension, at 280, the corresponding fastener 122, e.g. a set screw, is tightened to secure the tether 130 within the channel of the selected anchor device 120 with the corresponding vertebral body in position. For rigid curves, two pushers 110 can be used for translation in addition to the distal tensioning, such as shown in FIG. 2F.

According to another aspect of the presently disclosed subject matter, at 275, distraction and/or compression forces can be applied between two anchor devices 120 to force shortening of the corresponding vertebral segments 102, as shown in FIG. 3A-D. If significant wedging between two vertebral segments 102 occurs, local distraction or compression forces can be applied as needed to correct the segmental deformity. The use of compression and/or distraction can help achieve maximal correction. In some patients, the bottom few vertebral bodies 102 can be distracted out to reduce or prevent overcorrection.

In a similar manner, at 285, a modified thoracoscopic compressor 180 can be used to apply a compressive force between two adjacent anchor devices 120 to adjust the relative position between the corresponding vertebral body segments 102, as shown in an exemplary embodiment in FIGS. 4A-G. Additionally, a modified thoracoscopic distractor can be used to apply a distractive force between two adjacent anchor devices 120 to adjust the relative position between the corresponding vertebral body segments 102.

The modified thoracoscopic compressor 180 as shown in FIGS. 4A-G has the advantage of applying compressive forces between two vertebral body segments 102 through a 15 mm thoracoscopic portal. Additionally, the modified thoracoscopic distractor 180 has the advantage of applying distractive forces between two vertebral segments 102 through a 15 mm thoracoscopic portal. In some embodiments, distraction and/or compression between vertebral body segments 102 and tightening of the fasteners 122 can be performed with a modified thoracoscopic 182 distractor, further modified to include a screwdriver 184 integrally formed therewith, as shown for example in FIG. 4H.

The corrective processes of translation and tensioning, as well as compression and distraction as appropriate, are progressively repeated sequentially along each of the plurality of vertebral body segments 102 as needed (e.g. T7 to T11) until all of the fasteners 122 are tightened (e.g., from T6 to T11) to secure the tether 130 in their respective channels. The correction maneuvers are performed with fluoroscopic guidance and confirmation at each level.

Figure 7A:
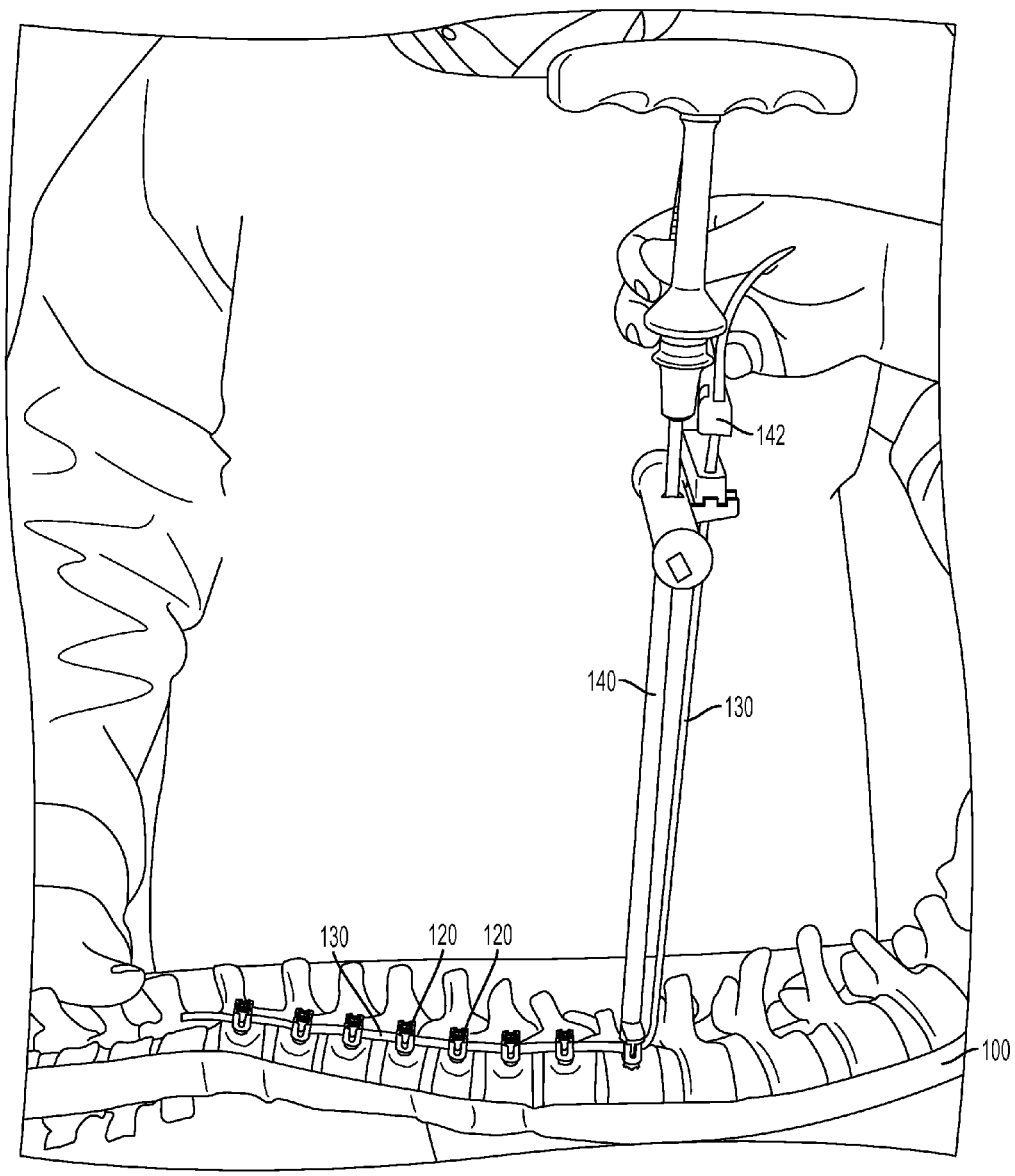
FIG. 7A demonstrates final tensioning of the tether in accordance with the disclosed subject matter.
Figure 7B:
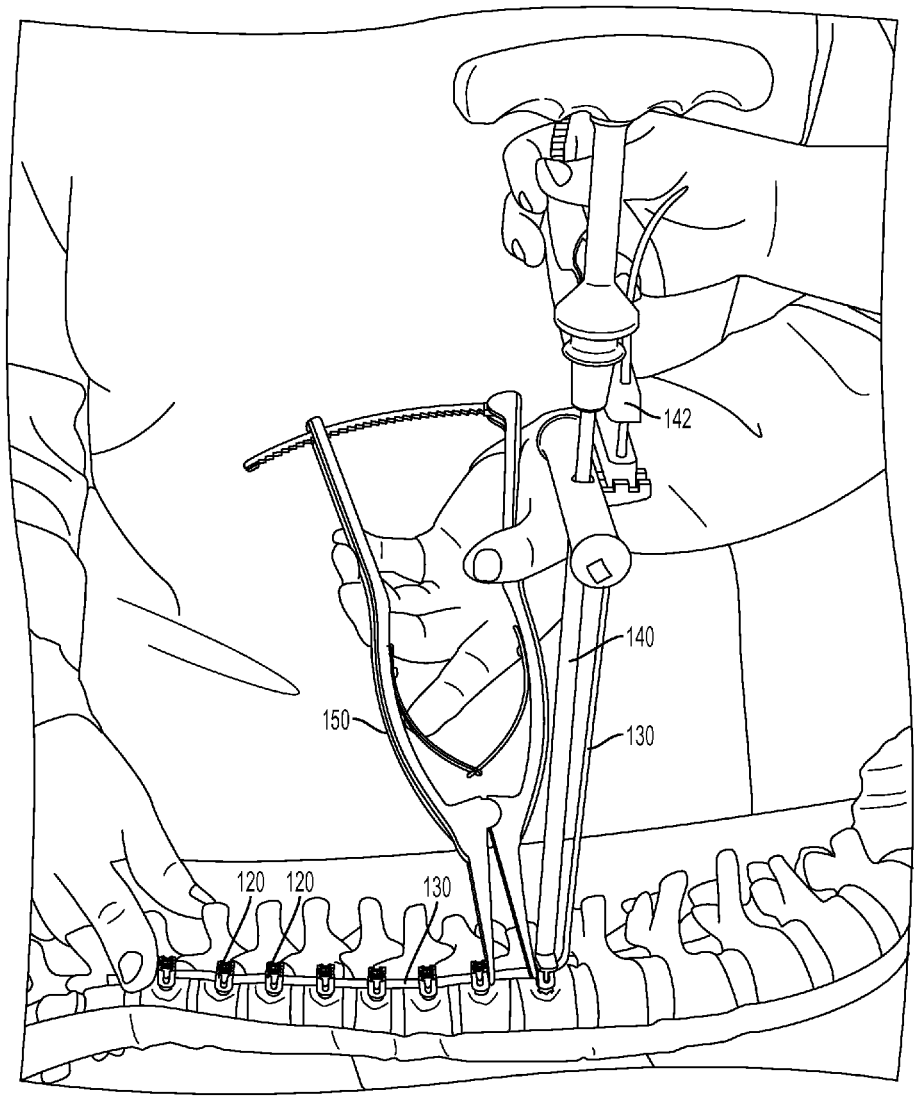
FIG. 7B demonstrates final tensioning using distraction to neutralize the T11-T12 segment in accordance with the disclosed subject matter.
Figure 7C:
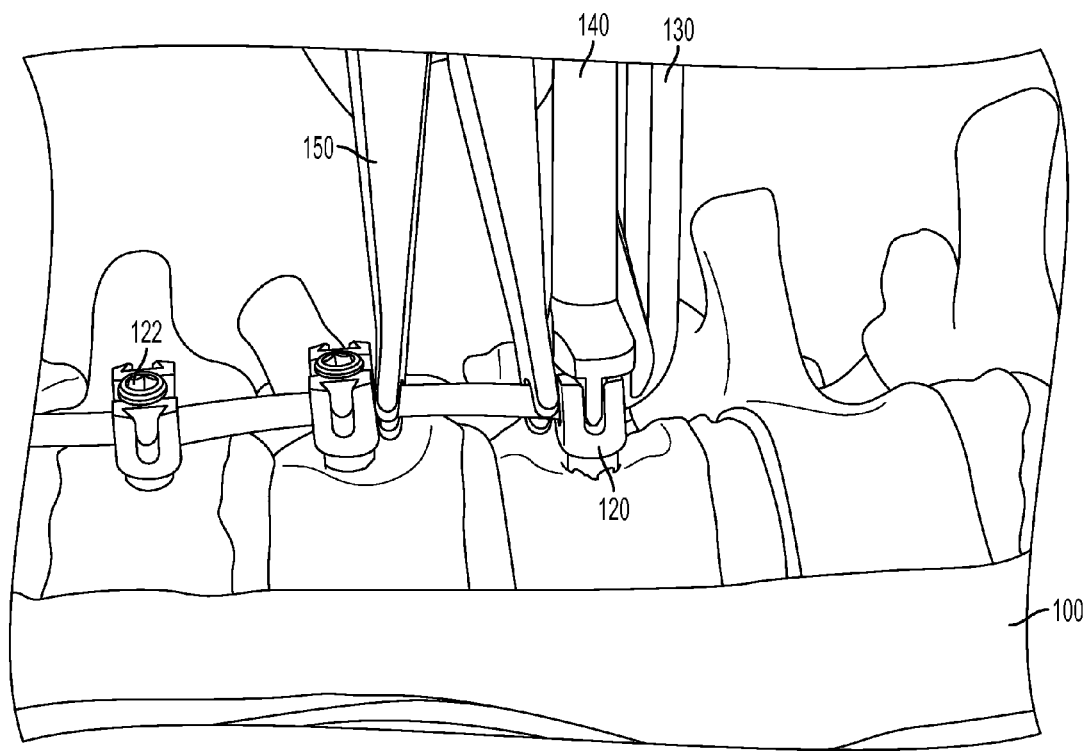
FIG. 7C is an enlarged view of FIG. 7B.

The tensioner 142 is then removed from T11 and engaged with the bottom-most anchor device 120 (e.g. T12), and the tether 130 is appropriately tensioned between T11 and T12, as shown in an exemplary embodiment in FIGS. 7A-C.

Figure 4A:
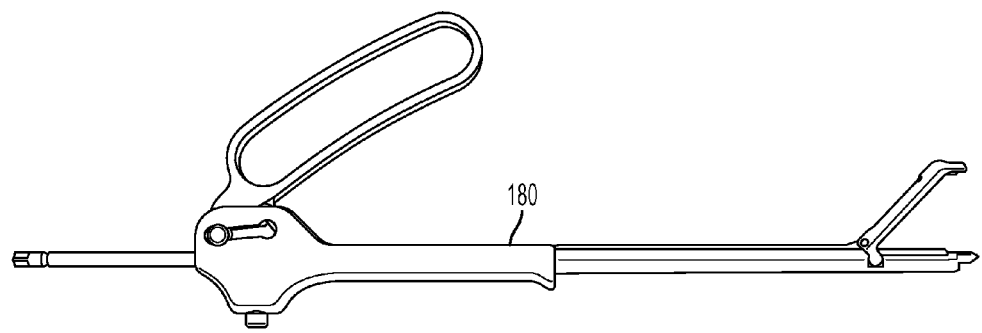
FIG. 4A is an image of a thoracoscopic compressor in an open position for use in accordance with the disclosed subject matter.
Figure 4B:
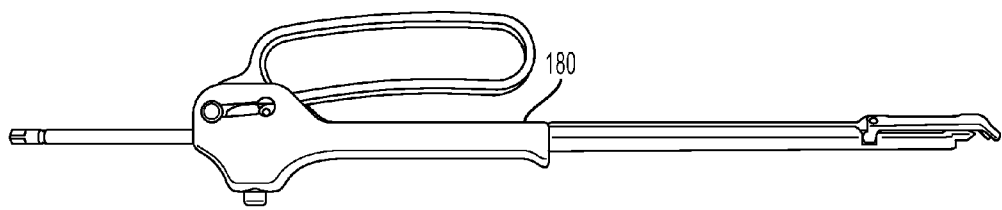
FIG. 4B is an image of a thoracoscopic compressor in a closed position for insertion through a port in accordance with the disclosed subject matter.
Figure 4C:
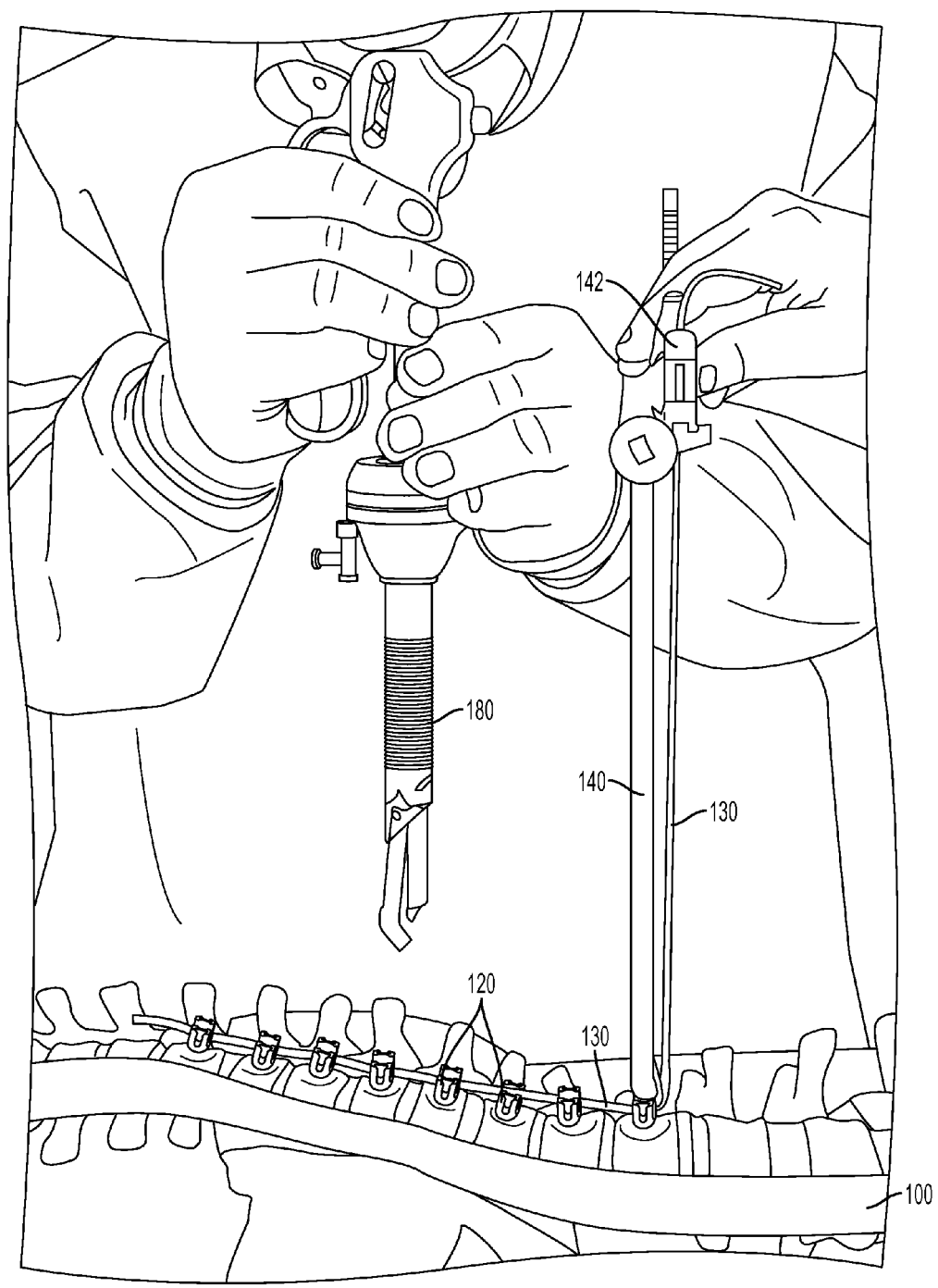
FIG. 4C demonstrates insertion of the compressor of FIG. 4B through a port in accordance with the disclosed subject matter.
Figure 4D:
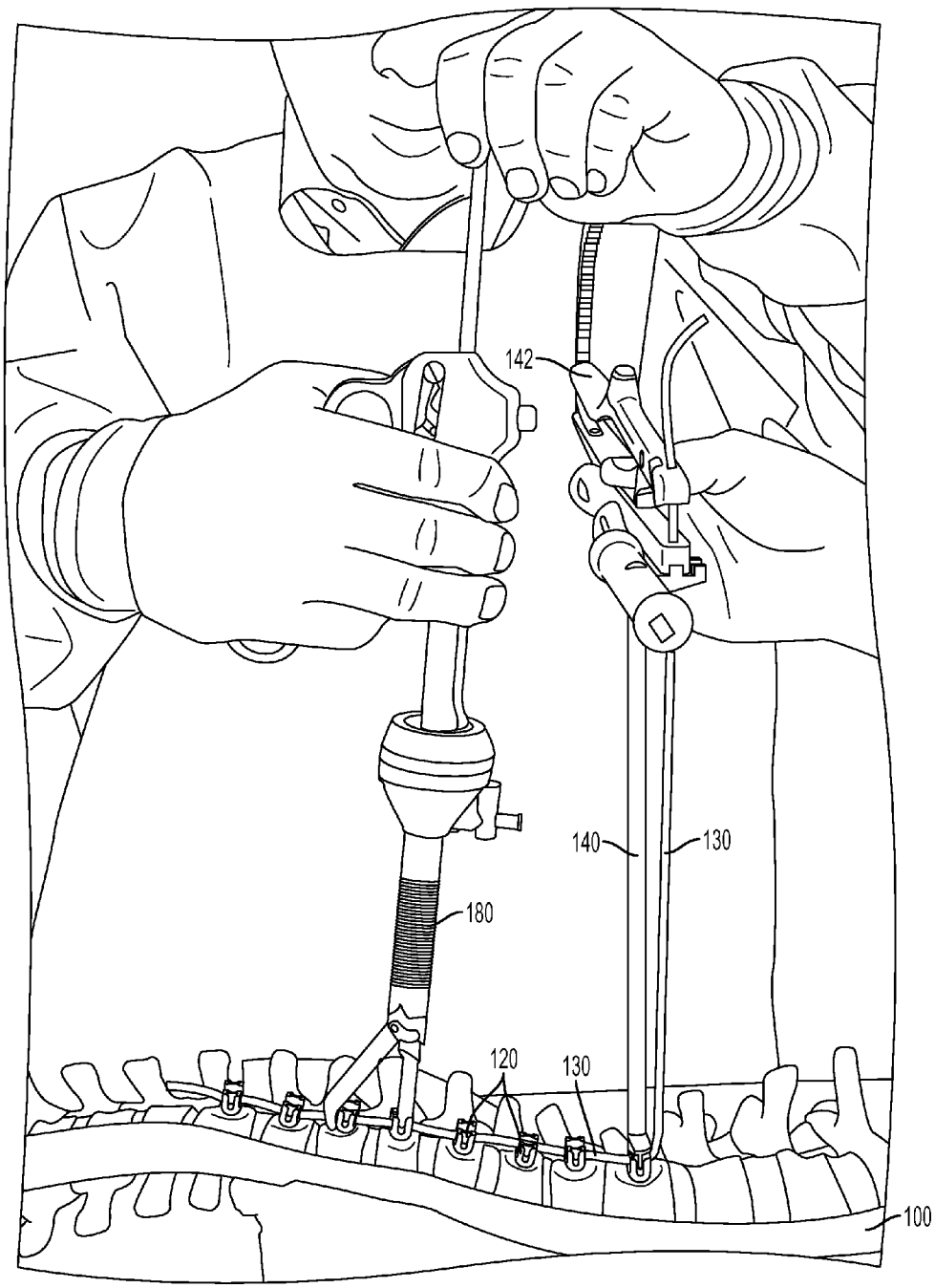
FIG. 4D demonstrates use of the compressor with the prongs in the anchor screw in accordance with the disclosed subject matter.
Figure 4E:
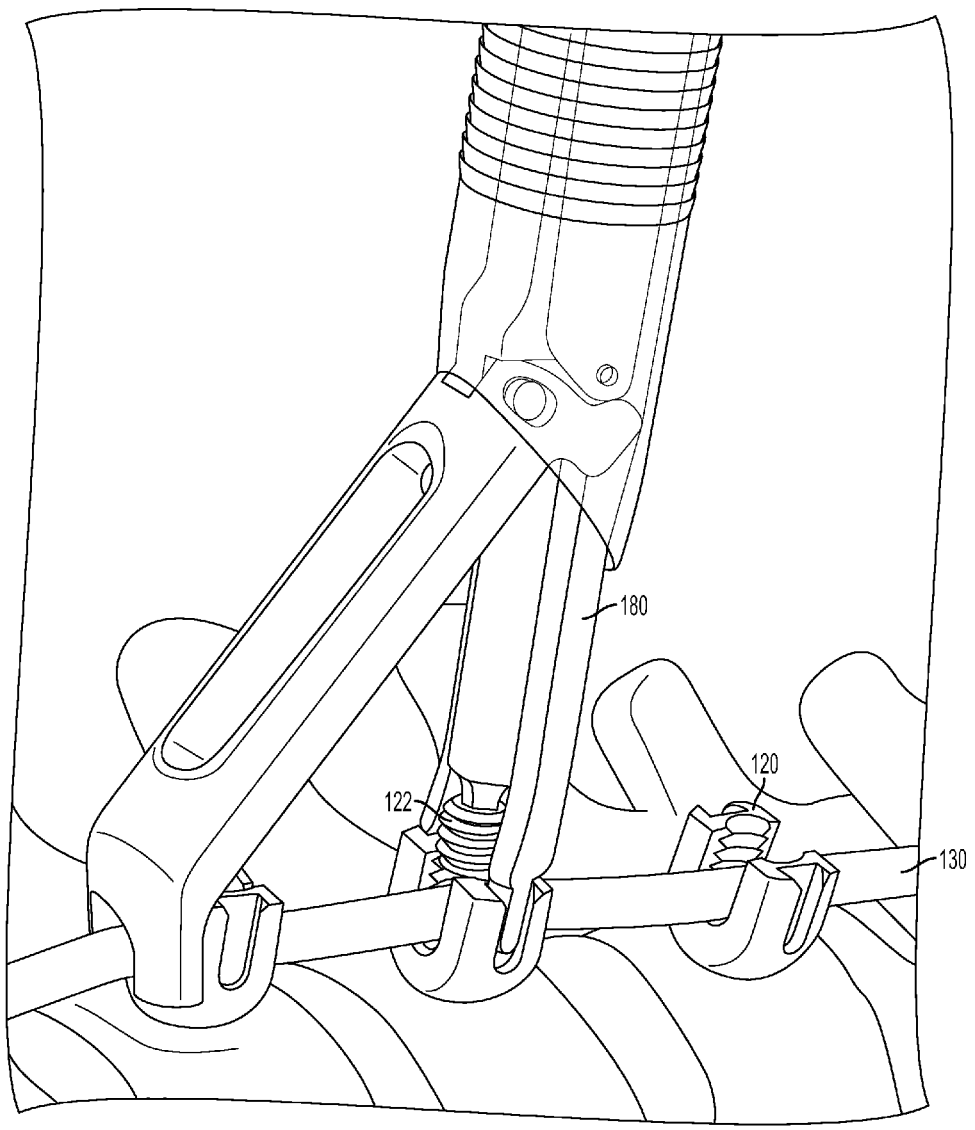
FIG. 4E is an enlarged view of FIG. 4D.
Figure 4F:
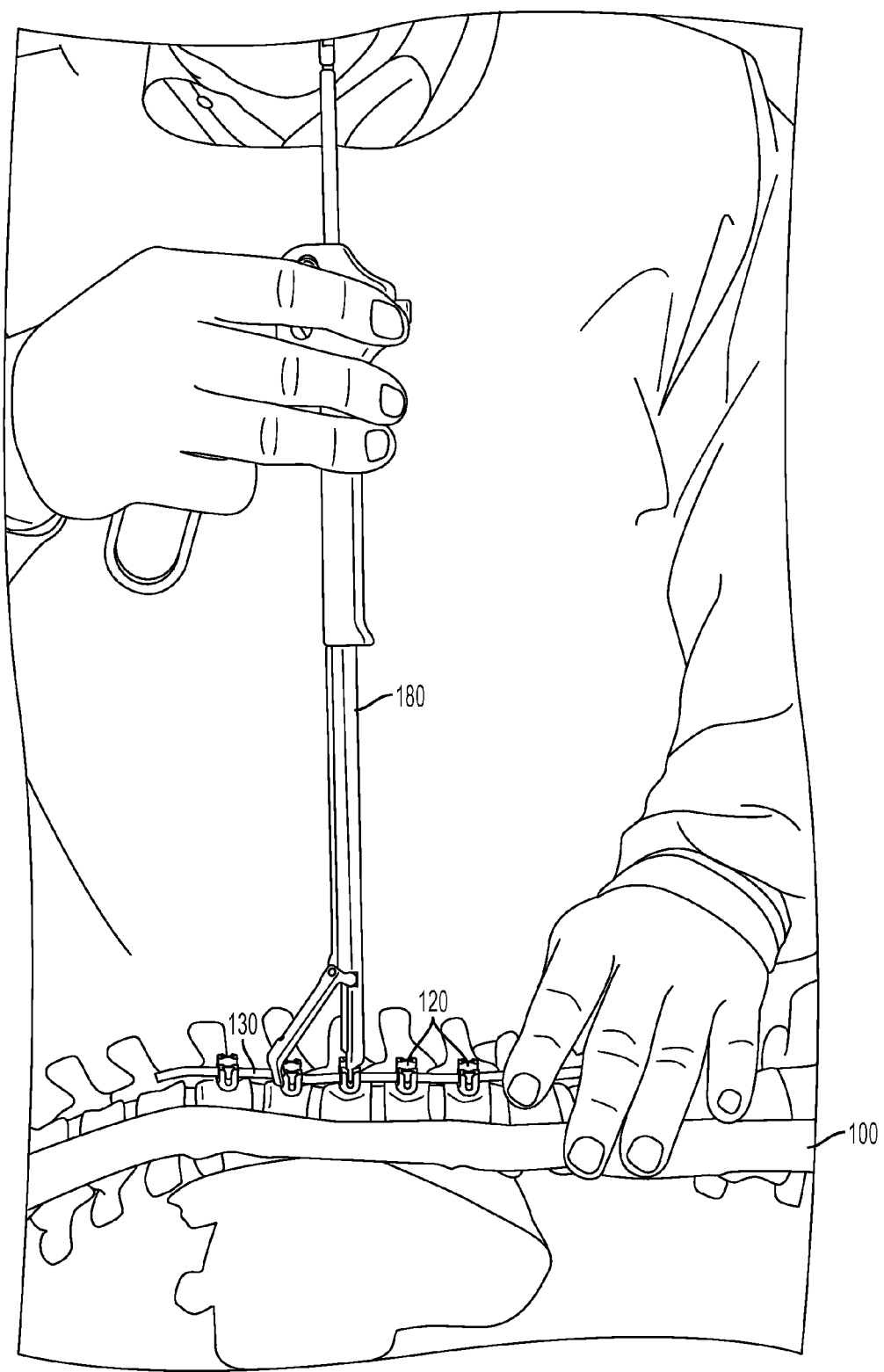
FIG. 4F demonstrates use of the compressor for a short spine segment (e.g. T6-T7) in accordance with the disclosed subject matter.
Figure 4G:
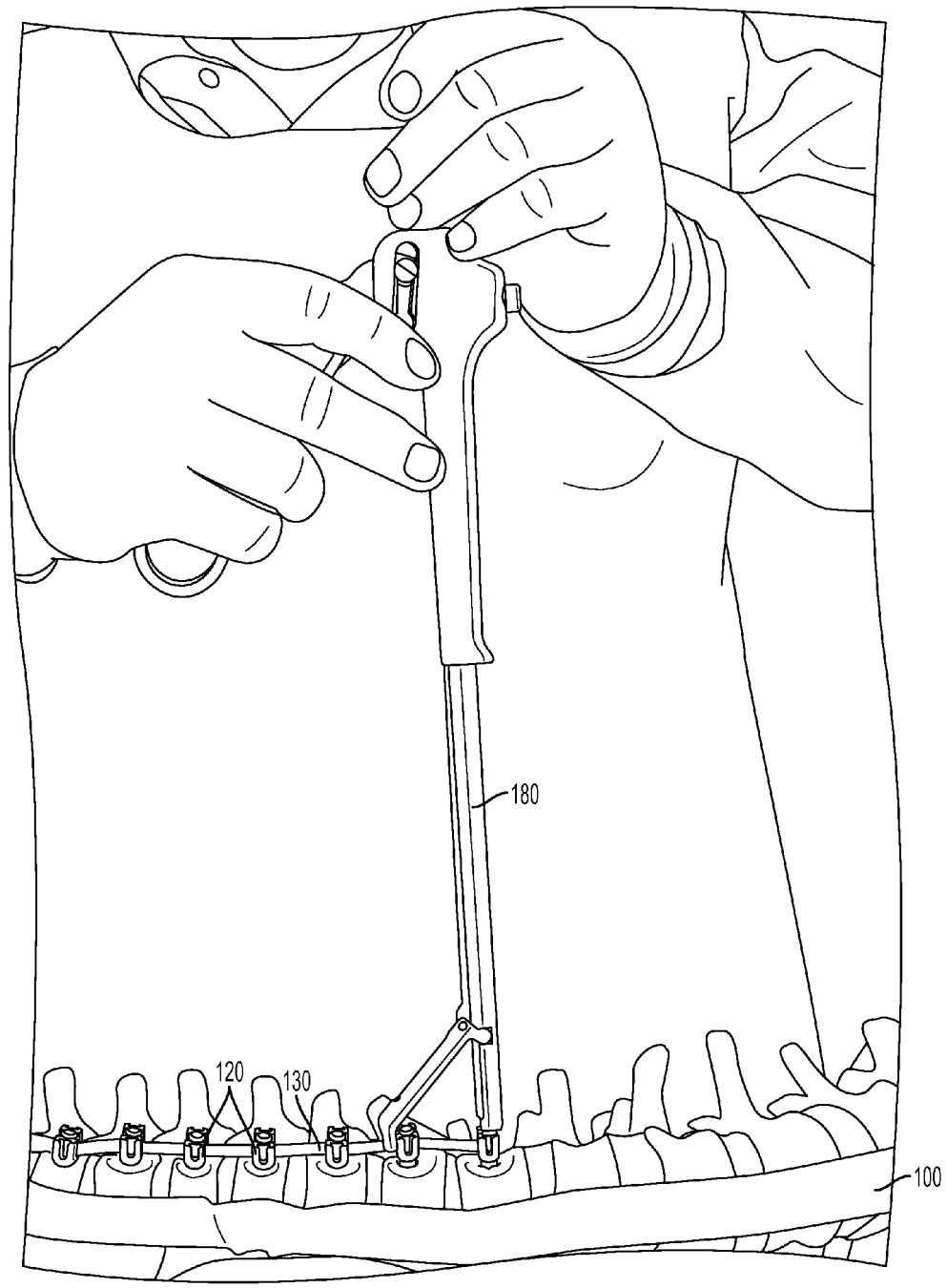
FIG. 4G demonstrates use of the compressor for a long spine segment (e.g. T11-T12) in accordance with the disclosed subject matter.
Figure 4H:
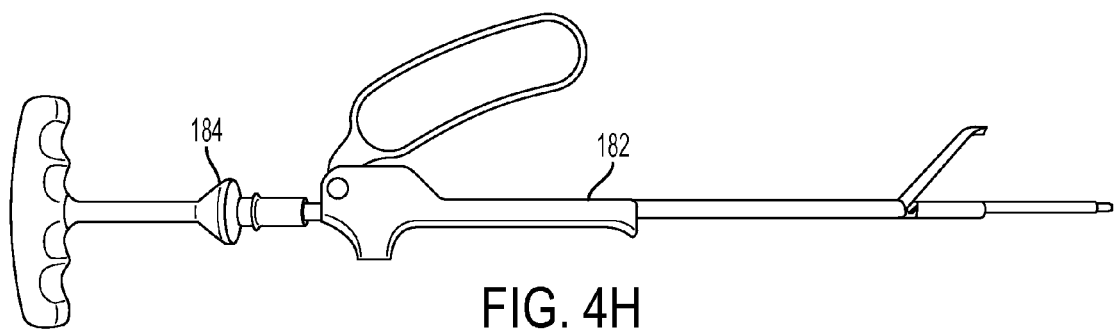
FIG. 4H is an image of an exemplary thoracoscopic compressor in an open position having a screwdriver formed integrally therewith.

If a segment, e.g. T11-T12, is wedged open on the convex side compression can be applied, either by the open compressor 175 (as such as shown in FIGS. 3D1 and 3D2) or the modified thoracoscopic compressor 180 (such as shown in FIG. 4E), to achieve correction.

As illustrated in FIG. 7A, if a vertebral body segment 102, e.g. T11-T12, is wedged closed on the convex side, distraction can be applied, either by the open distractor 170 (such as shown in FIGS. 7B-C) or by the modified thoracoscopic distractor 180 (such as shown in FIG. 5), to achieve correction.

The excess tether 130 at either end, e.g. above T6 and/or below T12, can cut utilizing an 11 blade knife, such as a Harmonic scalpel, introduced through the inferior portal and the excess pieces removed.

Figure 8A:
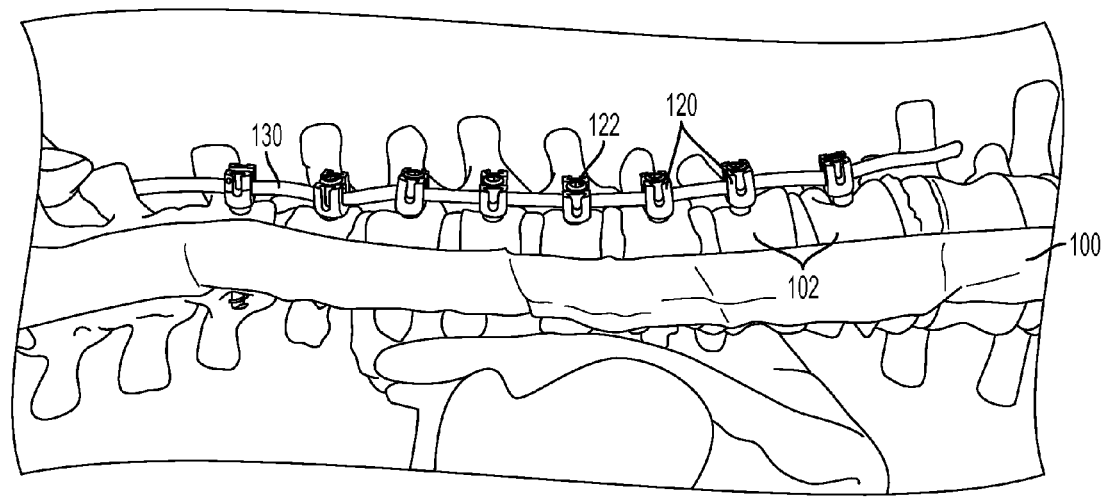
FIG. 8A demonstrates the final assembly with excess length of tether at the ends in accordance with the disclosed subject matter.
Figure 8B:
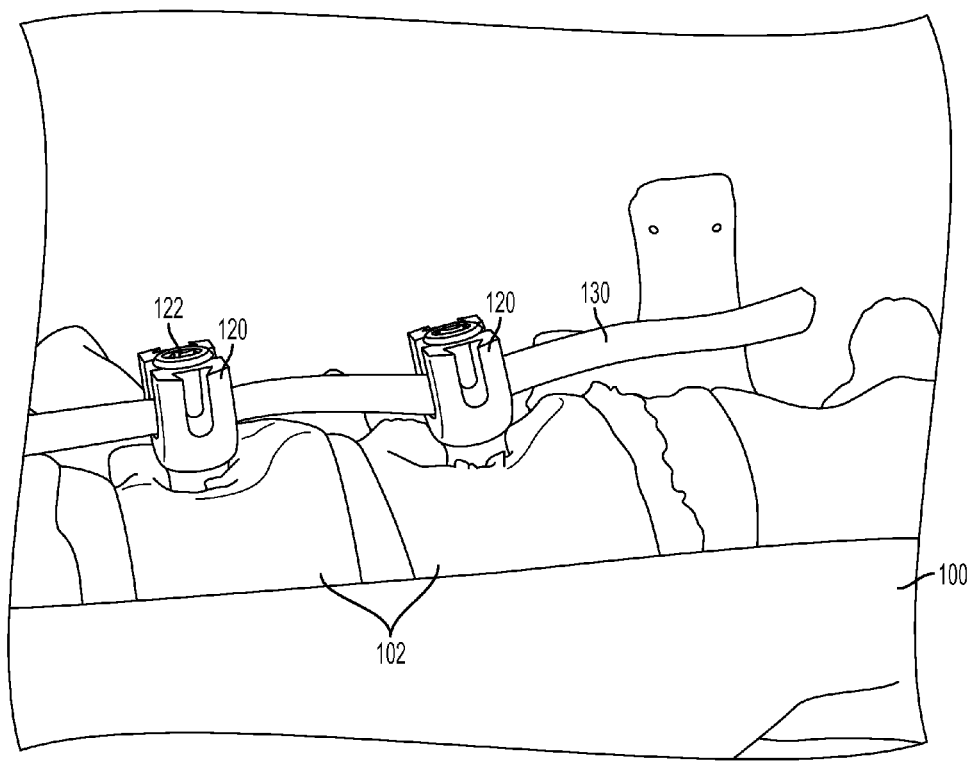
FIG. 8B is an enlarged view of FIG. 8A.

As desired, it can be beneficial to plan for grow of the patient and the ability to adjust the tether system to accommodate the best growth modulation of the spine 100. An excess length of e.g., 2-3 cm of the tether 130 can therefore remain beyond the inferior most anchor device 120 as shown in FIGS. 8A-B.

In another aspect of the disclosed subject matter, slack can be remain in the tether 130 between fasteners 122 in the lower vertebral body segments 102. In this manner, the tension in the tether 130 will not become excessive and cause overcorrection.

Figure 9A:
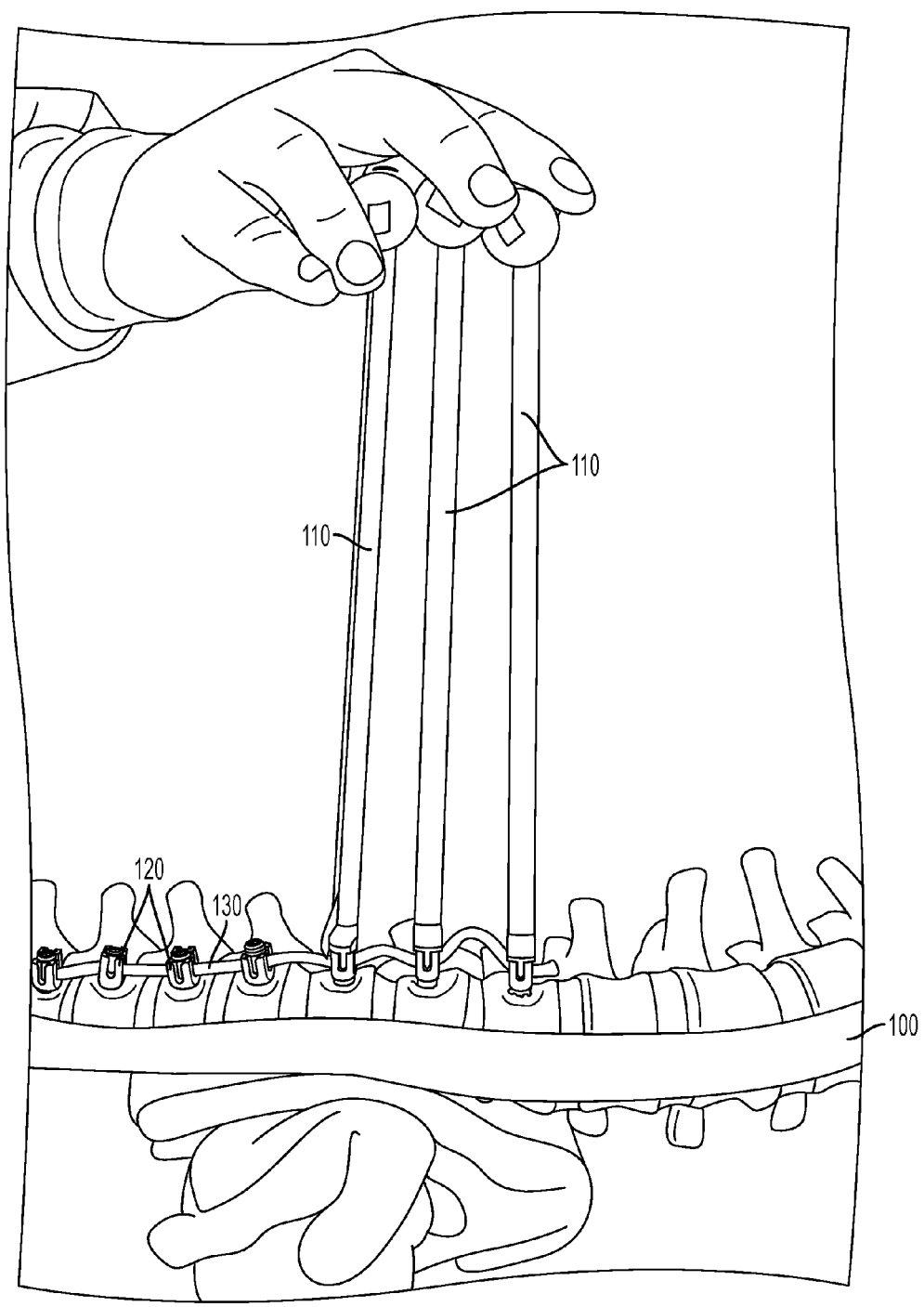
FIG. 9A demonstrates lengthening the tether for correction with growth in accordance with the disclosed subject matter.
Figure 9B:
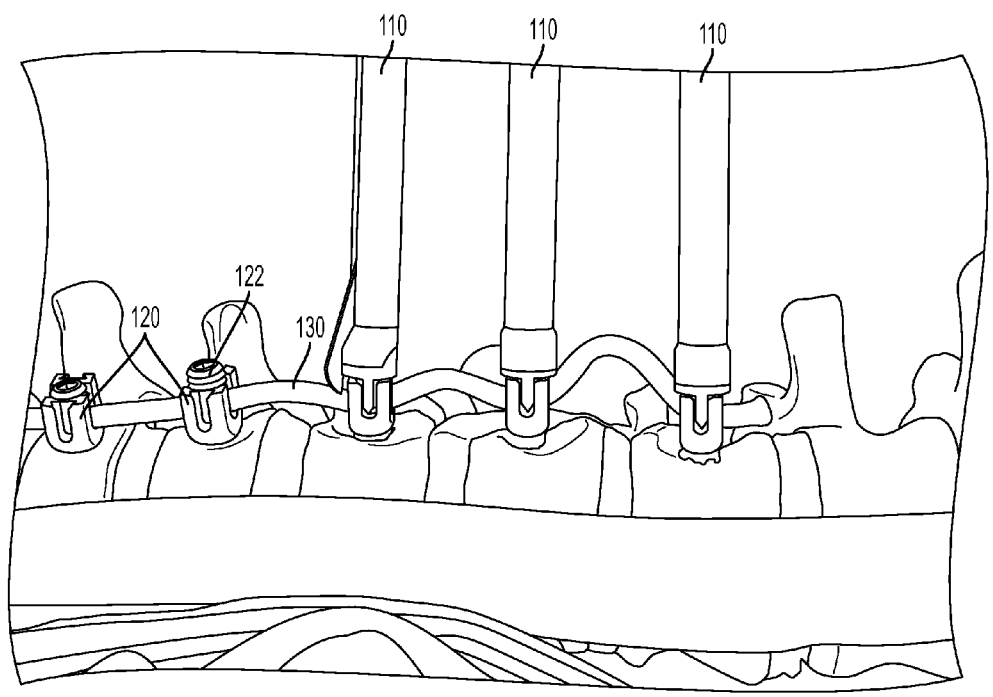
FIG. 9B is an enlarged view of FIG. 9A.
Figure 10:
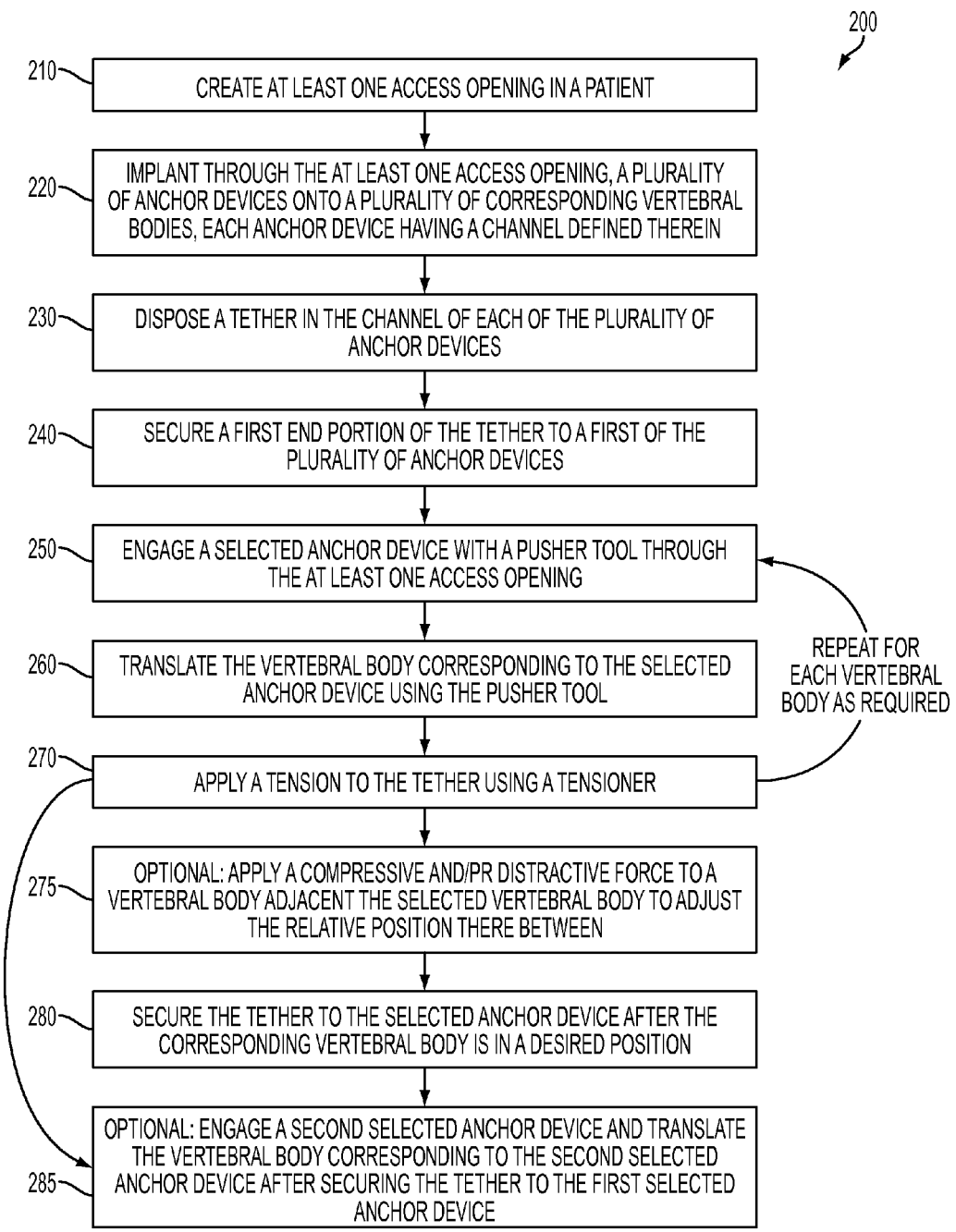
FIG. 10 is a schematic flow chart of the method in accordance with the disclosed subject matter.

If overcorrection of the spine occurs over months or years the surgeon can surgically lengthen the tether system, as shown in FIGS. 9A-B. Leaving extra length and or leaving slack in the tether 130 between two anchor devices 120 can allow for growth of the patient and the ability for the system to self-adjust, or to enable a subsequent surgical intervention without the need to repeat all of the surgery steps.

Upon completion, the access opening(s) in the patient can be closed in a conventional manner. For example, the pleura can then be closed using a 2-0 prolene, and a chest tube is passed through the inferior most 5-mm portal site in the anterior axillary line. The wounds are closed in standard manner utilizing 0-prolene, 2-0 prolene, and 3-0 monocryl.

Example 1

For purpose of illustration and confirmation of the disclosed subject matter, exemplary 2-year results of patients receiving treatment according to the techniques of the disclosed subject matter are provided. As discussed in more detail herein, 11 patients with thoracic IS (8 female) were identified, with a mean age of 12.3±1.6 years. Preoperatively, all were skeletally immature (Sanders mean=3.4±1.1, Risser mean=0.6±1.1). All underwent tethering of an average of 7.8±0.9 (range 7-9) levels with the most proximal being T5 and the most distal L2. Preoperative thoracic Cobb angle averaged 44.2±9.0° and corrected to 20.3±11.0° on first erect, with progressive improvement at 2 years (Cobb=13.5±11.6°, % correction=70%, p-value<0.00002). Similarly, the preoperative lumbar curve of 25.1±8.7° demonstrated progressive correction (first erect=14.9±4.9°, 2 year=7.2±5.1°, % correction=71%, p-value<0.0002). Thoracic axial rotation as measured by a scoliometer went from 12.4±3.3° preoperatively to 6.9±3.4° at the most recent measurement (p<0.01). Two patients returned to the operating room at 2 years postoperatively for loosening of the tether to prevent overcorrection.

In the example treatments discussed herein, the patients were placed in the lateral decubitus position with the curve side up (for example and as embodied here, right-side up). The first five patients underwent a mini thoracotomy at T9-10 to allow improved 3-D assessment of the anatomy and confirm safe bicortical screw placement. In alternative examples, the procedure has been performed thoracoscopically. Three 5-mm working thoracoscopic ports were placed in a triangular configuration with the apex at the fifth intercostal space (ICS) in the anterior axillary line and the base formed from two ports in the mid-axillary line, one in ICS 3 and the other in ICS 8. A camera was inserted into one port, a harmonic scalpel in another, and an endoscopic "peanut" in the third port to begin the dissection. The parietal pleura was incised along the lateral aspect of the vertebral bodies anterior to the rib heads in sequential fashion along the length of the curve. Proper position and vertebral levels were checked and confirmed using C-arm fluoroscopy in anteroposterior (AP) and lateral positions.

The pleura was incised for the length of spine to be tethered and reflected off the anterolateral aspect of the vertebral bodies on the convex side of the curve. The segmental vessels were identified, coagulated, and divided. Care was taken to reduce or prevent the disk spaces from being touched. A 15-mm working port was placed in the posterior axillary line to facilitate safe placement of vertebral body screws (embodied herein using 3 screws per incision). A 3-prong staple was placed on the anterior aspect of the vertebral body adjacent to the rib head. The position of the staple was confirmed using C-arm fluoroscopy in AP and lateral views. The staple was confirmed to be located anterior to the rib head, and positioning the staple proximate the foramen was avoided. Subsequently, the screw hole was tapped under fluoroscopic guidance aiming for the contralateral rib head. A suitable screw length was selected, and the screw was placed. Proper position was again checked and confirmed using C-arm fluoroscopy. The remaining screws were placed in a similar manner.

The tether was passed distal to proximal through the most caudal 15 mm port utilizing the working ports and placed into the screw heads. A tensioning device was placed on a caudal level screw and tensioned to remove any loose tether. Subsequently, utilizing a combination of apical translation, compression, and tensioning of the tether, the curvature of the spine was corrected as discussed herein, and the set screws were tightened to hold this correction. Fluoroscopy was utilized after each screw was engaged and tightened into the tether to confirm continued correction of the curvature. The tether was trimmed leaving approximately 2 cm of length on either side to accommodate potential future lengthening. A chest tube was placed through one of the 5-mm port sites, the hemithorax was irrigated, the lung reinflated under direct vision, and the incisions were closed in layers.

With reference to Table 1, of the 11 patients identified with 2-year follow-up, 8 were female, i.e., 73%. The mean age was 12.3±1.6 years. These patients were skeletally immature, with a mean Risser score of 0.6±1.1 and Sanders digital hand score 15 of 3.4±1.1.

TABLE 1

Patient Demographics and Skeletal Maturity

| | |
|---|---|
| Number of patients | 11 |
| Female | 8 |
| Mean age at surgery (years) | 12.3 ± 1.6 |
| Range | 10-15 |
| Avg. Risser score (range) | 0.6 ± 1.1 (0-3) |
| Avg. Sanders score (range) | 3.4 ± 1.1 (2-6) |

With reference to Table 2, patients underwent tethering of an average of 7.8±0.9 (range 7-9) levels, with the most proximal being T5 and most distal L2. Mean blood loss was 281 cc, with one outlier of 950 cc who was a patient in which visualization was difficult secondary to the lung not remaining collapsed. This was a patient in which a thoracic segmental vessel bled. Three patients underwent same day vertebral body stapling of their lumbar curves, as discussed herein. These patients had larger lumbar curves than those patients not stapled (pre-op lumbar curve stapled=35.3°, not stapled=21.2°). The mean OR time for the thoracic tether was 348 minutes. As embodied herein, increasing experience decreased the operative time from 362 minutes for the first 6 patients to 332 minutes for the last 5 patients.

TABLE 2

Perioperative Data

Surgical Procedure

| | | |
|---|---|---|
| Vertebral body Tethering | 8 (73%) | |
| Tethering + Lumbar Stapling | 3 (27%) | |
| | Mean | Median |
| Levels Tethered | 7.8 ± 0.9 | 8 |
| Operative Time (min) Tethering Only | 348 ± 44 | 352 |
| Operative Time (min) Tethering + VBS | 512 ± 69 | 476 |

TABLE 2-continued

Perioperative Data

| | | |
|---|---|---|
| EBL (cc) Tethering Only | 205 ± 161 | 113 |
| EBL (cc) Tethering + VBS | 483 ± 404* | 250 |

*One patient in the Tether + VBS group had a segmental bleed with a total EBL of 950 cc Referring now to Table 3, preoperative main thoracic Cobb angle averaged 44.2±9.0°, with a compensatory lumbar curve of 25.1±8.7° and a proximal thoracic curve of 21.2±10.8°. The mean percent flexibility of the thoracic curve was 57%. On first erect, these corrected to main thoracic 20.3±11.0°, lumbar 14.9±4.9°, and proximal thoracic 13.4±12.3°. By one year the values had improved to main thoracic 16.8±10.6°, lumbar 9.8±5.3°, and proximal thoracic 13.5±15.7°, with continued improvement observed at the 2-year time point (main thoracic 13.5±11.6°, lumbar 7.2±5.1°, and proximal thoracic 15.4±14.1°). Only one patient had a thoracic curve measuring >25°, and she was still skeletally immature.

TABLE 3

Coronal Measurements

| | Main Curve (°) | Lumbar Curve (°) | Proximal Curve (°) | Coronal Balance (cm) | Shoulder Angle (°) |
|---|---|---|---|---|---|
| Pre-op | 44.2 ± 9.0 | 25.1 ± 8.7 | 21.2 ± 10.8 | 1.6 ± 1.4 | 3.1 ± 1.8 |
| (range) | (34.0-66.0) | (7.8 ± 36.0) | (5.7-39.0) | (2.0-3.9) | (1.0-7.5) |
| 1$^{st}$ Erect | 20.3 ± 11.0 | 14.9 ± 4.9 | 13.4 ± 12.3 | 1.6 ± 1.6 | 2.7 ± 2.4 |
| (range) | (8.3-42.0) | (10.0 ± 26.0) | (0.7-31.0) | (5.0-5.9) | (0.0-7.3) |
| 24 mo. | 13.5 ± 11.6 | 7.2 ± 5.1 | 15.4 ± 14.1 | 1.3 ± 6.5 | 2.2 ± 2.3 |
| (range) | (−4.7-25.1) | (0.0 ± 15.8) | (0.0-32.6) | (2.0-20.4) | (0.0-5.8) |
| p-Value† | <0.00002 | <0.0002 | 0.01178 | 0.51 | 0.16 |

†Pre-op vs. 24 months

With reference to Table 4, the average preoperative thoracic kyphosis was 20.8±13.3°. Average preoperative thoracic kyphosis decreased to 13.5±8.7° on first erect and then gradually increased to 17.9±7.0° at one year and 21.6±12.7° at 2-year follow-up. The average preoperative lumbar lordosis was 47.5+10.6° and remained stable (54.9+13.1°) at 2 years. As such, no statistically significant change occurred in the sagittal measurements.

TABLE 4

Sagittal Measurements

| | Thoracic Kyphosis (°) | Lumbar Lordosis (°) | Sagittal Balance (cm) |
|---|---|---|---|
| Pre-op | 20.8 ± 13.3 | 47.5 ± 10.6 | 3.1 ± 2.0 |
| (range) | (1.7-46.0) | (38.0-65.0) | (0.3-7.9) |
| 1$^{st}$ Erect | 13.5 ± 8.7 | 38.4 ± 9.2 | 5.9 ± 3.8 |
| (range) | (0.2-30.0) | (30.0-57.0) | (0.1-11.9) |
| 24 mo. | 21.6 ± 12.7 | 54.9 ± 13.1 | 1.8 ± 0.9 |
| (range) | (4.9-37.6) | (45.2-69.8) | (0.6-2.9) |
| p-Value† | 0.13 | 0.66 | 0.10 |

†Pre-op vs. 24 months

Referring now to Table 5, overall the patients' thoracic scoliometer readings improved from a preoperative value of 12.4±3.3° to most recent value of 6.9±3.4°, p<0.01. Preoperatively all but one patient had a reading <10°, and by the 2-year follow-up, 9 out of 11 measured <10°.

TABLE 5

| Rib Rotation | |
|---|---|
| Pre-op (range) | 12.4 ± 3.3° (6-17) |
| Most recent (range) | 6.9 ± 3.4° (3-12) |
| p-Value | <0.01 |

Overall coronal (preoperative=1.6±1.4 cm, 2 year=1.3±6.5 cm, p-value=0.51) and sagittal balance (preoperative=3.1±2.0 cm, 2 year=1.8±0.9 cm, p value=0.1) remained stable. Similarly, shoulder balance did not significantly change (preoperative=3.1±1.8°, 2 years=2.2±2.3°, p-value=0.16), as shown for example in Tables 3 and 4.

No neurologic, infectious, or hardware related complications occurred. One patient had persistent atelectasis, which required a bronchoscopy. Two patients returned to the operating room for loosening of the tether secondary to overcorrection. The loosening included a thoracoscopic adjustment surgery where the distal three set screws were removed and the tension removed from the tether.

In the examples discussed herein, the safety and efficacy of the disclosed subject matter is illustrated. In the examples, the patients' coronal Cobb angles and thoracic prominences improved. No patient demonstrated a worsening of their deformity, and no neurologic, infectious, or hardware related complications occurred.

The examples described herein illustrate that the disclosed subject matter can be utilized in patients with thoracic scoliosis who are skeletally immature. In the patients discussed herein, the correction occurred progressively over time to imply growth modulation of the curve. The thoracic kyphosis increased over time in these patients. However, excessive kyphosis can be undesirable. To limit or prevent the potential hyperkyphosing effects of anterior surgery, a thoracic kyphosis>40° can be considered a contraindication for tethering surgery.

In the examples described herein, two patients underwent repeat surgery for overcorrection. It can be desirable to correct the curve to <20° intraoperatively, which can increase by 5-10° on first erect. However, patients with more growth potential may warrant less correction. In addition, the T9-L2 region in a flexible curve can be susceptible to overcorrection. As discussed herein, a second adjustment surgery can be performed, for example and without limitation, to compensate for overcorrection of >10°.

In the examples described herein, the results illustrate a gradual improvement of spine deformity with a low risk profile using the techniques of the disclosed subject matter.

Example 2

For purpose of illustration and confirmation of the disclosed subject matter, another example of treatment according to the techniques of the disclosed subject matter is provided. In this example, A twelve-year-and-five-month-old female presented with a right-sided, 34° main thoracic curve from T6-T12 and a lumbar curve of 34° from T12-L4. The patient's thoracic kyphosis was 22° (T5-T12). The patient had a Risser score of 0, and a Sanders score of 3. On lateral bending, flexibility of the thoracic curve measured 12° and the lumbar curve measured 2.3°. On forward bending, the patient's thoracic rotation and lumbar prominence both measured 10°.

The patient was anesthetized and positioned in the lateral decubitus position with the right side up. Two small working thoracoscopic portals were made in the anterior axillary line. A 15-mm working portal and a small thoracotomy incision were also made on the mid axillary line. The anterior spine was prepared with stripping the pleura circumferentially around the spine and transection of the segmental vessels at the vertebral levels that would be instrumented. A 3-prong staple was impacted into place on the anterior aspect of the vertebral bodies just anterior to the rib head under C-arm guidance. Screw holes were drilled and tapped and screw length estimated. 5.0 or 6.0-millimeter diameter Dynesys screws were placed along the length of the construct from T6 to T12. A flexible PET tether (Zimmer Dynesys, Raytham, Mass.) was placed through the thoracotomy site into the screw head of the superior most screw, which was secured with a set screw. The tether was sequentially placed into all of the additional screw heads. Tension was placed on the tether through a custom tensioning device placed on T11 (one level proximal from the end instrumented vertebra so as to not cause screw loosening). Careful reduction translation force was placed onto the spine at the apical screw simultaneously as the tether was tensioned and the set screw tightened at T7. The surgery progressed in a similar fashion distally with the tether sequentially tensioned and then attached to each screw via a set screw progressing proximally to distally to T12. The tether was trimmed leaving 2.5 cm extra tether beyond the proximal and distal screw for future adjustment (e.g., lengthening) if needed.

The wound was closed, a chest tube inserted, and the patient was turned to a right lateral decubitus position. Anterior stapling of the lumbar curve was performed from T12 to L3. Stapling of L3-4 was avoided, at least in part because it can be unnecessary for curve control and can involve significant retraction on the psoas muscle. Global imaging of the spine in both AP and lateral views was performed, and visual confirmation of significant reduction of the curvature in the coronal plane and appropriate alignment in the sagittal plane was obtained.

The thoracic main curve measured 11° intraoperatively while the patient was in the supine position in the operating room. Prior to discharge the patients curve measured 15° on the first erect x-ray. Follow up x-rays were obtained at 6 weeks, 3 months, 6 months, 12 months, 18 months and 2 years. With reference to Table 6, the patient's films showed progressive correction of the coronal deformity over the course of the follow up period. The thoracic curve measured 13° at the 6-week follow up, 10° at 3 months, 6° at six months. At the 12-month follow up, the patient's main thoracic curve measured 0°, representing a 100% correction. However, between 12 and 18 months, the patient's main thoracic curve began to overcorrect. At 18 months her main thoracic curve measured −14°. At this time, the patient was still thought to have some residual growth remaining. As such, at 21 months after her index surgery, the decision was made to adjust the tether.

During the adjustment procedure, the most distal 3 levels of the tether were loosened and distraction techniques were applied to the spine. As discussed herein, during the index surgery, the tether was trimmed leaving 2.5 cm extra tether beyond the distal screw, which allowed for the adjustment. After the tether was loosened and suitable correction was attained, intraoperative films were taken. The patient's main curve measured 0° intraoperatively and 1° at first erect. At the 24-month, follow-up, the curve measured −2.7°.

TABLE 6

Radiographic Data

| Follow Up | Main Curve | Lumbar Curve | Proximal Curve | Thoracic Kyphosis | Lumbar Lordosis | Rib Rotation |
|---|---|---|---|---|---|---|
| Pre-op | 34° | 34° | 6° | 21° | 34° | 10° |
| 1st Erect | 15° | 16° | 12° | 16° | 20° | — |
| 1.5 mo | 13° | 22° | 5° | 24° | 41° | — |
| 3 mo | 10° | 23° | 3° | 18° | 37° | 3° |
| 6 mo | 6° | 16° | 3° | 22° | 33° | 5° |
| 12 mo | 0° | 11° | 0° | 23° | 41° | 5° |
| 18 mo | −14° | 6° | 0° | — | — | 3° |
| 24 mo | −3° | 6° | 0° | 30° | 31° | 4° |

With reference to Table 6, the patient's preoperative proximal and lumbar curves measured 5.7° (T1-T4) and 34° (T10-L4), respectively. At first erect, the proximal curve measured 12° and the lumbar curve measured 16°. At the 24-month follow up, the proximal curve measured 0° and the lumbar curve measured 6.3°. In the sagittal plane, the patient's preoperative thoracic kyphosis measured 32° (T4-T12), and her lumbar lordosis measured 34° (L1-L5). At first erect, kyphosis was measured at 16° and lordosis at 20°. At the 24-month follow up, the patient's thoracic kyphosis measured 17° and her lumbar lordosis measured 31°.

While the disclosed subject matter is described herein in terms of certain preferred embodiments, those skilled in the art will recognize that various modifications and improvements can be made to the disclosed subject matter without departing from the scope thereof. For example, additional features and modifications as appropriate are disclosed in U.S. Pat. Nos. 6,616,669, 6,296,643 and U.S. Patent Publication 2010/0106195, each of which is incorporated reference herein in its entirety.

Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A method for performing spinal correction surgery, comprising: creating at least one access opening in a patient; implanting, through the at least one access opening, a plurality of anchor devices onto a plurality of corresponding vertebral bodies, with each anchor device anterior of a respective vertebral body rib head, each anchor device having a channel defined therein; disposing a tether in the channel of each of the plurality of anchor devices; securing a first end portion of the tether to a first of the plurality of anchor devices; engaging a selected anchor device with a pusher tool through the at least one access opening; translating the vertebral body corresponding to the selected anchor device using the pusher tool; applying a tension to the tether using a tensioner; and cutting the tether with an excess length of tether greater than a distance between two adjacent anchor devices extending beyond an inferior most anchor device.

2. The method of claim 1, wherein the at least one access opening comprises a portal.

3. The method of claim 2, wherein the portal is a thoracoscopy portal.

4. The method of claim 2, wherein the at least one access opening comprises a plurality of portals.

5. The method of claim 1, wherein the plurality of anchor devices comprise a plurality of spine screws.

6. The method of claim 5, wherein each spine screw includes a threaded shank portion and a head portion, the channel of each spine screw is disposed proximate the head portion.

7. The method of claim 5, wherein each spine screw includes a fastener to secure the tether in the channel thereof.

8. The method of claim 1, wherein the tether is made of polyethylene-terephthalate (PET).

9. The method of claim 1, wherein securing the tether to the first anchor device comprises fastening the tether within the channel of the first anchor device.

10. The method of claim 1, wherein applying the tension to the tether is performed at a second portion of the tether.

11. The method of claim 1, wherein translating the corresponding vertebral body and applying the tension to the tether are performed simultaneously to produce a corrective force.

12. The method of claim 1, wherein the pusher is a thoracoscopic vertebral body pusher.

13. The method of claim 1, further comprising: applying a compressive force to a vertebral body adjacent the selected vertebral body to adjust the relative position therebetween.

14. The method of claim 1, further comprising: applying a distractive force to a vertebral body adjacent the selected vertebral body to adjust the relative position therebetween.

15. The method of claim 1, further comprising: securing the tether to the selected anchor device after the corresponding vertebral body has been translated to a desired position.

16. The method of claim 15, further comprising: engaging a second selected anchor device with a pusher tool through the at least one access opening; translating the vertebral body corresponding to the second selected anchor device using the pusher tool.

17. The method of claim 16, wherein engaging the selected second anchor device and translating the vertebral body corresponding to the selected second anchor device are performed after securing the tether to the first selected anchor device.

18. The method of claim 1, further comprising securing a second end portion of the tether to a last of the plurality of anchor devices.

19. The method of claim 1, further wherein slack is maintained in the tether between at least two anchor devices.

* * * * *